(12) United States Patent
Riordan

(10) Patent No.: US 8,895,299 B2
(45) Date of Patent: Nov. 25, 2014

(54) METHOD FOR EXPANSION OF STEM CELLS

(75) Inventor: Neil H. Riordan, Tempe, AZ (US)

(73) Assignee: XON Cells, Inc., Germantown, MD (US)

( * ) Notice: Subject to any disclaimer, the term of this patent is extended or adjusted under 35 U.S.C. 154(b) by 0 days.

(21) Appl. No.: 12/823,960

(22) Filed: Jun. 25, 2010

(65) Prior Publication Data

US 2010/0261152 A1   Oct. 14, 2010

Related U.S. Application Data

(63) Continuation of application No. 11/353,692, filed on Feb. 14, 2006, now abandoned.

(60) Provisional application No. 60/653,390, filed on Feb. 15, 2005.

(51) Int. Cl.
| | |
|---|---|
| *C12N 5/0789* | (2010.01) |
| *C12N 5/02* | (2006.01) |
| *A61Q 7/00* | (2006.01) |
| *A61Q 19/08* | (2006.01) |
| *A61K 35/28* | (2006.01) |
| *A61K 35/50* | (2006.01) |
| *A61K 35/48* | (2006.01) |
| *A61K 35/44* | (2006.01) |
| *C12N 5/00* | (2006.01) |
| *A61K 8/98* | (2006.01) |
| *A61K 38/18* | (2006.01) |

(52) U.S. Cl.
CPC . *A61K 8/982* (2013.01); *A61Q 7/00* (2013.01); *A61Q 19/08* (2013.01); *A61K 35/28* (2013.01); *C12N 2502/02* (2013.01); *A61K 35/50* (2013.01); *A61K 35/51* (2013.01); *A61K 35/44* (2013.01); *C12N 5/0018* (2013.01); *A61K 38/1825* (2013.01)
USPC .......................... 435/325; 435/384; 435/404

(58) Field of Classification Search
CPC ............. C12N 5/0647; C12N 2501/10; C12N 2501/20; C12N 2502/025; C12N 5/0018; C12N 2501/125; C12N 2501/145; C12N 2501/23; C12N 2501/26; C12N 5/0605; C07K 14/52; A61K 2300/00; A61K 35/50; A61K 35/51; A61K 38/20
USPC .................................. 424/93.7; 435/325, 404
See application file for complete search history.

(56) References Cited

U.S. PATENT DOCUMENTS

| | | |
|---|---|---|
| 3,862,002 A | 1/1975 | Sanders |
| 5,871,464 A | 2/1999 | Tryggvason et al. |

(Continued)

FOREIGN PATENT DOCUMENTS

WO   WO 2004046312 A2 *   6/2004

OTHER PUBLICATIONS

Bug, et al., "Valproic Acid Stimulates Proliferation and Self-renewal of Hematopoietic Stem Cells" *Cancer Research* (2005) 65(7): 2537-2541.

(Continued)

*Primary Examiner* — Taeyoon Kim
(74) *Attorney, Agent, or Firm* — Knobbe Martens Olson & Bear LLP

(57) ABSTRACT

A method of increasing the growth of stem cells by mixing the stem cells with a growth medium that has been conditioned by an incubation with placental tissue. The method increases the expansion of the stem cell population.

6 Claims, No Drawings

(56) References Cited

U.S. PATENT DOCUMENTS

| | | | |
|---|---|---|---|
| 7,255,879 | B2 | 8/2007 | Hariri |
| 2002/0142397 | A1* | 10/2002 | Collas et al. ............... 435/69.5 |
| 2005/0008614 | A1 | 1/2005 | Nieland et al. |
| 2005/0058631 | A1 | 3/2005 | Kihm et al. |
| 2005/0090004 | A1* | 4/2005 | Sayre ........................... 435/366 |
| 2005/0148034 | A1 | 7/2005 | Hariri et al. |

OTHER PUBLICATIONS

Burgess, et al., "Stimulation by Human Placental Conditioned Medium of H emopoietic Colony Formation by Human Marrow Cells" *Blood* (1977) 49: 573-583.

Carpenter, et al., "Characterization and Differentiation of Human Embryonic Stem Cells" *Cloning and Stem Cells* (2003) 5: 79-88.

Cerdan, et al., "VEGF-$A_{165}$ augments erythropoietic development form human embryonic stem cells" *Blood* (2004) 103(7): 2504-2512.

Chadwick, et al., "Cytokines and BMP-4 promote hematopoietic differentiation of human embryonic stem cells" *Blood* (2003) 102(3): 906-915.

Chivu, et al., "Ex vivo differentiation of umbilical cord blood progenitor cells in the presence of placental conditioned medium" *J. Cell Mol. Med.* (2002) 6(4): 609-620.

Cong, Yu-Sheng and Silvia Bacchetti, "Histone Deacetylation is Involved in the Transcriptional Repression of *hTERT* in Normal Human Cells" *J. Bio. Chem.* (2000) 275(46): 35665-35668.

Danet, et al., "Expansion of human SCID-repopulating cells under hypoxic conditions" *J. Clin. Invest.* (2003) 112: 126-135.

De Felice, et al., "Histone Deacetylase Inhibitor Valproic Acid Enhances the Cytokine-Induced Expansion of Human Hematopoietic Stem Cells" *Cancer Res.* (2005) 65(4): 1505-1513.

Ezashi, et al., "Low $O_2$ tensions and the prevention of differentiation of hES cells" *PNAS* (2005) 102(13): 4783-4788.

Ferrero, et al., "Trophoblast Cell Line Conditioned Medium for in Vitro Culture and Antigenic Characterization of Acute Myeloid Leukemia Clonogenic Cells" *Cancer Research* (1987) 47: 6413-6417.

Gagnon, et al., "Interaction of 5-aza-2'-deoxycytidine and depsipeptide on antineoplastic activity and activation of 14-3-3σ, E-cadherin and tissue inhibitor of metalloproteinase 3 expression in human breast carcinoma cells" *Anti-Cancer Drugs* (2003) 14: 193-202.

Gekas, et al., "The Placenta is a Niche for Hematopoietic Stem Cells" *Developmental Cell* (2005) 8: 365-375.

Hou, et al., "The Histone Deacetylase Inhibitor Trichostatin A Derepresses the Telomerase Reverse Transcriptase (*hTERT*) Gene in Human Cells" *Experimental Cell Research* (2002) 274: 25-34.

Ivanovic, et al., "Hypoxia maintains and interleukin-3 reduces the pre-cology-forming cell potential of dividing $CD34^+$ murine bone marrow cells" *Experimental Hematology* (2002) 30: 67-73.

Kijima, et al., "Trapoxin, an Antitumor Cyclic Tetrapeptide, Is an Irreversible Inhibitor of Mammalian Histone Deacetylase" *J. Bio. Chem.* (1993) 268(30): 22429-22435.

Köhler, et al., "Defining Optimum Conditions for the Ex Vivo Expansion of Human Umbilical Cord Blood Cells. Influences of Progenitor Enrichment, Interference with Feeder Layers, Early-Acting Cytokines and Agitation of Culture Vessels" *Stem Cells* (1999) 17: 19-24.

Laharrague, et al., "High expression of leptin by human bone marrow adipocytes in primary culture" *FASEB J.* (1998) 12: 747-752.

Lee, et al., "Histone Deacetylase Activity is Required for Embryonic Stem Cell Differentiation" *Genesis* (2004) 38: 32-38.

Lohrmann, et al., "Human Placenta-conditioned Medium for Stimulation of Human Granulopoietic Precursor Cell (CFU-C) Colony Growth in vitro" *Blut.* (1978) 36: 81-88.

Mukhopadhyay, et al., "Histone deacetylation is directly involved in desilencing the expression of the catalytic subunit of telomerase in normal lung fibroblast" *J. Cell. Mol. Med.* (2005) 9(3): 662-669.

Munsie, et al., "Isolation of pluripotent embryonic stem cells from reprogrammed adult mouse somatic cell nuclei" *Current Biology* (2000) 10: 989-992.

Peters, et al., "Comparative Effects of Granulocyte-Macrophase Colony-Stimulating Factor (GM-CSF) and Granulocyte Colony-Stimulating Factor (G-CSF) on Priming Preipheral Blood Progenitor Cells for Use with Autologous Bone Marrow After High-Dose Chemotherapy" *Blood* (1993) 81(7): 1709-1719.

Petzer, et al., "Self-renewal of primitive human hematopoietic cells (long-term-culture-initiating cells) in vitro and their expansion in defined medium" *PNAS* (1996) 93: 1470-1474.

Reik, et al., "Epigenetic Reprogramming in Mammalian Development" *Science* (2001) 293: 1089-1093.

Sato, et al., "Maintenance of Pluripotency in human and mouse embryonic stem cells through activation of Wnt signaling by a pharmacological GSK-3-specific inhibitor" *Nature Medicine* (2004) 10(1): 55-63.

Shav-Tal, Yaron, and Dov Zipori, "The Role of Activin A in Regulation of Hemopoiesis" *Stem Cells* (2002) 20: 493-500.

Taketazu, et al., "Clonal Growth of Human Acute Myeloid Leukemia Cells (ML-1 and HL-60) in Serum-free Agar Medium" *Cancer Research* (1984) 44: 531-535.

Thalmeier, et al., "Establishment of Two Permanent Human Bone Marrow Stromal Cell Lines with Long-term Post Irradiation Feeder Capacity" *Blood* (1994) 83(7): 1799-1807.

Trowbridge, et al., "Glycogen synthase kinase-3 is an in vivo regulator of hematopoietic stem cell repopulation" *Nature Medicine* (2006) 12(1): 89-98.

Yamaguchi, et al., "Serum-free coculture system for ex vivo expansion of human cord blood primitive progenitors and SCID mouse-reconstituting cells using human bone marrow primary stromal cells" *Experimental Hematology* (2001) 29: 174-182.

Young, et al., "Inhibitors of histone deacetylases promote hematopoietic stem cell self-renewa" *Cytotherapy* (2004) 6(4): 328-336.

Zhang, Jiwang, and Linheng Li, "BMP signaling and stem cell regulation" *Developmental Biology* (2005) 284: 1-11.

Placental Structure and Classification (2008) http://www.vivo.colostate.edu/hbooks/pathphys/reprod/placenta/structure.html.

International Search Report and Written Opinion dated Jun. 27, 2008, issued in Int'l App. No. PCT/US06/05170.

\* cited by examiner

METHOD FOR EXPANSION OF STEM CELLS

CROSS-REFERENCE TO RELATED APPLICATIONS

This application is a continuation of U.S. application Ser. No. 11/353,692, entitled METHOD FOR EXPANSION OF STEM CELLS, which was filed on Feb. 14, 2006, which claimed priority under 35 U.S.C. §119 to U.S. Provisional Application No. 60/653,390, which was filed on Feb. 15, 2005; the disclosure of each of which is hereby incorporated by reference in its entirety.

FIELD OF THE INVENTION

This invention relates to the field of stem cell technology. More particularly, the invention describes a new method for increasing the growth of stem cells by mixing the stem cell culture with a medium that has been incubated with placental tissue.

BACKGROUND OF THE INVENTION

Stem cells have the ability to divide for indefinite periods in culture and to give rise to specialized cells. Typically, stem cells are divided into two main groups: adult stem cells and embryonic stem cells. Stem cells may also be generated through artificial means such as nuclear transfer, cytoplasmic transfer, cell fusion, parthenogenesis and reprogramming. Isolated stem cells can give rise to many types of differentiated cells, and can be used to treat many types of diseases.

Adult stem cells are undifferentiated but are present in differentiated tissues, and are capable of differentiation into the cell types from the tissue that the adult stem cell originated. Adult stem cells have been derived from various sources, such as the nervous system (McKay, 1997, *Science* 276:66-71; Shihabuddin, et al., 1999, *Mol. Med Today* 5:474-480); bone marrow (Pittenger, et al., 1999, *Science* 284:143-147; Pittenger, M. F. and Marshak, D. R. (2001) In: Mesenchymal stem cells of human adult bone marrow. Marshak, D. R., Gardner, D. K., and Gottlieb, D. eds. (Cold Spring Harbor, N.Y.: Cold Spring Harbor Laboratory Press) 349-374); adipose tissue (Gronthos, et al., 2001, *J Cell. Physiol.* 189:54-63), dermis (Toma, et al., 2001, *Nature Cell Biol.* 3:778-784); pancreas and liver (Deutsch, el al., 2001, *Development* 128: 871-881). Stem cells have also been isolated from umbilical cord (Rogers, et al., 2004, *Best Pract Res Clin Obstet Gynaecol.* 18(6):893-908; Wang et al., 2004, *Stem Cells* 22(7):1330-1337; Surbek, et al, 2002, *Ther Umsch.* 59(11):577-582; and placenta (Yen et al., 2005, *Stem Cells* 23(1):3-9), each of which is incorporated by reference herein in its entirety. It is believed that stem cells of the adult type are also found in smooth muscle tissue, striated muscle tissue, cardiac muscle tissue, bone tissue, bone spongy tissue, cartilage tissue, pancreatic ductal tissue, spleen tissue, thymus tissue, tonsil tissue, Peyer's patch tissue, lymph nodes tissue, thyroid tissue, epidermis tissue, dermis tissue, subcutaneous tissue, heart tissue, lung tissue, vascular tissue, endothelial tissue, blood cells, bladder tissue, kidney tissue, digestive tract tissue, esophagus tissue, stomach tissue, small intestine tissue, large intestine tissue, adipose tissue, uterus tissue, eye tissue, lung tissue, testicular tissue, ovarian tissue, prostate tissue, connective tissue, endocrine tissue, and mesentery tissue.

Several patents disclose various aspects of adult stem cells. For example, U.S. Pat. No. 5,556,783 discloses methods of culturing hair follicle stem cells, while U.S. Pat. No. 5,486,359 discloses methods of isolating human mesenchymal stem cells. U.S. Pat. Nos. 4,714,680, 5,061,620, and 5,087,570 provide examples of hematopoietic stem cells. Each of these patents is incorporated by reference herein in its entirety.

Embryonic stem cells are undifferentiated cells derived from the embryo. Typically these cells are extracted from the inner cell mass of a blastocyte and when cultured under the unique conditions, either alone or in combination with a variety of feeder cells, the embryonic stem cells maintain euploid karyotype, do not undergo senescence, and retain the ability to differentiated into cells of the endodermal, ectodermal, and mesodermal lineages.

These cells have the potential to become a wide variety of specialized cell and tissue types, which can then be used for basic research, drug discovery, and treatment (or prevention) of many types of diseases. Patents describing aspects of embryonic stem cells include U.S. Pat. No. 6,506,574 to Rambhatla, U.S. Pat. No. 6,200,806 to Thomson, U.S. Pat. No. 6,432,711 to Dinsmore, and U.S. Pat. No. 5,670,372 to Hogan, each of which is incorporated by reference herein in its entirety. Importantly, murine embryonic stem cells can be cultured indefinitely under the presence of leukemia inhibitory factor (LIF), which maintains their undifferentiated state. In contrast, human embryonic stem cells are not responsive in the same manner to LIF, thus stimulating the invention of numerous methodologies to expand them. Unfortunately, many such methodologies involve the use of either murine feeder cells or other animal components, hence limiting the therapeutic potential of these cells. Furthermore, even when established cell lines, such as the federally approved embryonic stem cells, are cultured in murine-free conditions, contamination is still present as recently reported (Martin, et al., 2005, *Nat Med* 11:228-232, which is incorporated by reference herein in its entirety). Accordingly, one object of the invention disclosed is to provide novel methods of expanding stem cells in absence of animal components, said invention being applicable to a variety of stem cells, including embryonic stem cells.

The importance of technologies associated with expansion of stem cells, both of adult and/or embryonic derivation is illustrated by the numerous preclinical and clinical uses of these cells in treatment of a wide range of diseases.

One of the earliest clinical uses of stem cells was for performing bone marrow transplants in patients with hematological malignancies in which hematopoietic stem cells derived from the donor bone marrow were administered into the recipient subsequent to providing said recipient with a sufficient dose of radiation and/or chemotherapy in order to ablate not only the hematological malignancy but also non-malignant hematopoiesis. The administration of, non-malignant hematopoietic stem cells resulted in donor-specific hematopoiesis and in some patients, cure of the malignancy. This was first described by Thomas et al in 1957, who reported that large volumes of donor bone marrow could be safely infused in patients with acute leukemia following myeloablation and that donor-specific hematopoiesis was established (Thomas, et al., 1957, *N Engl J Med* 257:491-496, which is incorporated by reference herein in its entirety). The identification of similar hematopoietic stem cell activity in the peripheral blood led to development of techniques used to mobilize and harvest peripheral blood hematopoietic stem cells for use in transplantation settings. For example, the use of GM-CSF and G-CSF in enhancing the number of peripheral blood hematopoietic stem cells was reported in the clinical situation of autologous transplantation subsequent to high dose chemotherapy (Peters, et al., 1993, *Blood* 81:1709-1719; Sheridan, et al., 1992, *Lancet* 339:640-644, each of which is incorporated by reference herein in its entirety).

In addition to treatment of hematological malignancies, stem cells have been utilized in the context of therapy for solid tumors. The dose limiting variable in cancer chemotherapy is bone marrow toxicity. Accordingly, in 1958, Kurnick et al performed an autologous bone marrow transplant to demonstrate ability of infused bone marrow to allow use of very high doses of chemotherapy and/or radiation therapy (Kurnick, et al., 1958, *Ann Intern Med* 49:973-986, which is incorporated by reference herein in its entirety). The use of autologous hematopoietic cell transplants combined with high dose chemo/radiotherapy for solid tumors has been extensively investigated for breast (Peppercorn, et al., 2005, *Cancer* 104: 1580-1589; Dillman, et al., 2005, *Am J Clin Oncol* 28:281-288), colon (Leff, et al., 1986, *J Clin Oncol* 4:1586-1591; Franchi, et al., 1994, *Eur J Cancer* 30A:1420-1423), lung (Ziske, et al., 2002, *Anticancer Res* 22:3723-3726), nasopharyngeal cancer (Chen, et al., 2003, *Jpn J Clin Oncol* 33:331-335), and other types of cancers (Gratwohl, et al., 2004, *Ann Oncol* 15:653-660), each of which is incorporated by reference herein in its entirety.

The identification of the type 1 transmembrane protein/adhesion molecule, the sialomucin CD34 as a marker of hematopoietic stem cells led to the use of CD34+ cell selection as a means of concentrating hematopoietic stem cell activity (Civin, et al., 1984, *J Immunol* 133:157-165, which is incorporated by reference herein in its entirety). Specifically, it was demonstrated that although bone marrow mononuclear cells contain approximately 1-4% CD34+ cells, the administration of these cells, but not bone marrow depleted of CD34+ cells, into lethally irradiated baboons led to hematopoietic reconstitution (Berenson, et al., 1988, *J Clin Invest* 81:951-955, which is incorporated by reference herein in its entirety). Clinical development of purified CD34+ cells as a source of stem cells was originally sought as a method of performing bone marrow transplant without contamination of donor T cells. This would in theory stop development of graft versus host disease, one of the main causes of allogeneic transplant associated morbidity and mortality (Ferrara, et al., 2005, *Clin Adv Hematol Oncol* 3:415-419, 428, which is incorporated by reference herein in its entirety). Unfortunately, clinical evidence demonstrated that patients receiving purified CD34+ stem cell grafts, although having a lower incidence of graft versus host disease, also had a higher incidence in leukemic relapse due to an immunologically mediated graft versus leukemia effect that is absent when donor bone marrow grafts are depleted of T cells (Martino, et al., 2000, *Haematologica* 85:1165-1171; Butt, et al., 2003, *Leuk Lymphoma* 44:1509-1513, each of which is incorporated by reference herein in its entirety). The critical importance of bone marrow derived T cells in the induction and upkeep of graft versus leukemia effects was illustrated in studies of leukemic patients who have relapsed and were subsequently treated by infusion of donor T cells. This induced a long-term remission in the patients that had major relapse (Kolb, H. J., 1998, *Vox Sang* 74 Suppl 2:321-329; Guglielmi, et al., 2002, *Blood* 100:397-405, each of which is incorporated by reference herein in its entirety). Furthermore, it was also observed that under some conditions, bone marrow derived non-CD34 cells of the osteoblast lineage have a role in facilitating engraftment in allogeneic settings (Good, R. A., 2000, *World J Surg* 24:797-810, which is incorporated by reference herein in its entirety). Despite these potential drawbacks, clinical use of CD34+ cells both from mobilized peripheral blood, as well as bone marrow, during autologous transplantation for high dose chemo/radiation therapy was considered to be a useful approach (Korbling, et al., 2001, *Blood* 98:2900-2908; Pecora, et al., 2001, *Bone Marrow Transplant* 27:1245-1253; Pecora, A. L., 1999, *Bone Marrow Transplant* 23 Suppl 2:S7-12, each of which is incorporated by reference herein in its entirety). This is due to the fact that in this setting, neither facilitator cells are needed, since the graft is autologous, and the CD34+ selection substantially clears the marrow of contaminating tumor cells, so that the risk of tumor relapse is lessened as opposed to using non-purified bone marrow (Preti, et al., 2001, *Cytotherapy* 3:85-95; Siena, et al., 2000, *J Clin Oncol* 18:1360-1377; Vannucchi, et al., 1998, *Br J Haematol* 103:610-617, each of which is incorporated by reference herein in its entirety).

The use of hematopoietic stem cells has also been described for "reprogramming" the immune system to induce an antigen-specific state of non-responsiveness called tolerance. Specifically, this use can be divided into two main areas: the use of stem cells to induce donor-specific tolerance during allogeneic or xenogeneic transplantation, and the use of stem cells to induce tolerance in situations of autoimmunity. Although common mechanisms of tolerance maintenance such as generation of T regulatory cells, effector T cell depletion, and effector T cell anergy have been described in both types of tolerance, the mechanism of induction seems to be different; therefore we will describe them individually.

The possibility of bone marrow hematopoietic stem cells having the utility of inducing tolerance to a grafted organ was first elaborated on by Owens in the 1940s. In studies demonstrating that in utero mixing of blood in the context of shared circulation between two genetically different cows, he observed bilateral transplantation tolerance in adulthood. Accordingly, he postulated that the original sharing of circulation may have contributed to the state of tolerance which theoretically should not have existed due to the genetic disparity between the siblings. Furthermore, definitive roles for using stem cells to induce tolerance came from Billingham and Medawar in the 1950s in experiments showing injection of donor bone marrow cells into neonates allowed for tolerance to the donor antigen when the animal reached adulthood (Slavin, S., 2002, *Int J Hematol* 76 Suppl 1:172-175, which is incorporated by reference herein in its entirety). In animal models it has been demonstrated that bone marrow cells contribute to generation of a donor-specific tolerogenic state which is associated with chimeric hematopoiesis. The combination of donor-specific bone marrow transplant, with solid organs, has been used in some clinical situations to induce complete tolerance to the grafted organ without the need for chronic, continuous immune suppression (George, et al., 2002, *Immunol Res* 26:119-129, which is incorporated by reference herein in its entirety). Unfortunately, wide spread use of bone marrow induced tolerance is limited by the fact that bone marrow transplantation is associated with a high degree of morbidity and mortality during the myeloablative phase. In addition, the possibility of graft versus host disease is another pitfall to the full-scale implementation. In order to overcome this, several methods of inducing partial chimerism, or mini-chimerism are being investigated through the use of non-myeloid ablative techniques such as donor-specific transfusions combined with anti CD154 antibodies (Seung, et al., 2003, *J Clin Invest* 112:795-808, which is incorporated by reference herein in its entirety). Induction of organ tolerance by hematopoietic stem cells is believed to occur through both thymic dependent (Noris, et al., 2001, *J Am Soc Nephrol* 12:2815-2826, which is incorporated by reference herein in its entirety), and independent (van Pel, et al., 2003, *Transpl Immunol* 11:375-384, which is incorporated by reference herein in its entirety) mechanisms. Specifically, donor hematopoietic cells generate a variety of both lymphoid and non-lymphoid cells that express the same antigens found in the donor organ, but somehow redirect the immune system not to attack these specific antigens, while maintaining responses against other antigens not related to the graft. One mechanism that is postulated to occur is the thymic stromal tissue in the recipient becomes populated with donor-derived cells. These cells then act at the level of negative selection in order to induce apoptosis of T cells reactive to the donor antigen in a similar way to which the immune system deletes autoreactive T cells during thymic selection (Shizuru, et al., 2000, *Proc Natl Acad Sci USA* 97:9555-9560, which is incorporated by reference herein in its entirety). Another mechanism of tolerance involves the persistent presentation of donor antigen in absence of costimulatory molecules. This was demonstrated in one situation by the fact that persistence of T cells from the donor bone marrow is essential in maintaining tolerance (Xu, et al., 2004, *J Immunol* 172:1463-1471, which is incorporated by reference herein in its entirety). The mesenchymal component of the bone marrow produces a cell population that consitutively secretes immune inhibitory factors such as IL-10 and TGF-b while presenting antigens (Liu, et al., 2004, *Transplant Proc* 36:3272-3275; Togel, et al., 2005, *Am J Physiol Renal Physiol* 289:F31-42, each of which is incorporated by reference herein in its entirety). This is believed to further inhibit immunity in an antigen specific manner. During T cell activation, two general signals are required for the T cell in order to mount a productive immune response, the first signal is recognition of antigen, and the second is recognition of costimulatory or coinhibitory signals. Mesenchymal cells present antigens to T cells but provide a coinhibitory signal, thus specifically inhibiting T cells that recognize them, and other cells expressing similar antigens. Finally, the fact that CD34+ cells express the T cell killing molecule FasL has been postulated as another mechanism of tolerogenesis. Indeed transplantation of bone marrow from mice with a mutated FasL did not induce tolerogenesis in recipients (George, et al., 1998, *Nat Med* 4:333-335, which is incorporated by reference herein in its entirety).

The potential of using hematopoietic cell transplantation for autoimmunity derives from the belief that the immune system can be deleted and recapitulated, but in such a manner to "reset the clock" so that autoreactive T cells will not reappear (Muraro, et al, Renewing the T cell repertoire to arrest autoimmune aggression. *Trends Immunol.*, e-published on Jan. 4, 2006, which is incorporated by reference herein in its entirety). Specifically, it is known that the process of autoimmunity requires the failure of several self-tolerance mechanisms before clinical presentation appears. These include: a) self-reactive T cell deletion in the thymus; b) anergy/deletion of self reactive T cells in the periphery; c) failure of the regulatory T cell activity; and d) the presence of inflammation or antigen release in order to allow expansion of the autoreactive T cell clone. During autoimmunity the failure of all of these systems is usually a culmination of environmental and genetic factors occurring over a protracted period of time. Accordingly if the immune system could be made to "start anew" the normal tolerogenic processes would again be reactivated and the disease would be cured, at least temporarily. To date clinical use of autologous stem cells has been performed for a variety of autoimmune indications, including rheumatoid arthritis (Jantunen, et al., 1999, *Scand J Rheumatol* 28:69-74, which is incorporated by reference herein in its entirety), multiple sclerosis (Karussis, et al., 2004, *J Neurol Sci* 223:59-64; Brodsky, et al., 1999, *Curr Opin Oncol* 11:83-86, each of which is incorporated by reference herein in its entirety), systemic lupus erythromatosis (Brunner, et al., 2002, *Arthritis Rheum* 46:1580-1584; Burt, et al., 2006, *Jama* 295:527-535, each of which is incorporated by reference herein in its entirety), and systemic sclerosis (Viganego, et al., 2000, *Curr Rheumatol Rep* 2:492-500, which is incorporated by reference herein in its entirety). According to a report in 2005, approximately 700 patients in total have received an autologous stem cells for autoimmune diseases with a positive benefit/risk ratio that has led to initiation of phase III prospective randomized controlled trials (Tyndall, et al., 2005, *Clin Exp Immunol* 141:1-9, which is incorporated by reference herein in its entirety).

Induction of tolerance through hematopoietic stem cell transplantation, either from bone marrow or peripheral blood sources possesses the intrinsic danger of bone marrow failure during ablation of the recipient immune system. Although non-myeloablative protocols are under development, even these carry the risk of immune suppression due to the lymphoablation. Accordingly there is a need in the art to develop novel methods of either expanding hematopoietic stem cells ex vivo in large enough quantities to guarantee graft take, as well as methods of in vivo expanding the stem cells and their progeny so that the period under which the transplant recipient is immunosuppressed is minimized.

Stem cell therapy has also been performed in the context of administration of mesenchymal stem cells, without the hematopoietic component, for induction of tolerance. It was demonstrated in a murine model that flk-1+Sca-1-mesenchymal cell transplantation leads to permanent donor-specific immunotolerance in allogeneic host and results in long-term allogeneic skin graft acceptance (Deng, et al., 2004, *Exp Hematol* 32:861-867, which is incorporated by reference herein in its entirety). Other studies have shown that mesenchymal stem cells are inherently immunosuppressive through production of PGE-2, interleukin-10 and expression of the tryptophan catabolizing enzyme indoleamine 2,3,-dioxygenase as well as Galectin-1 (Kadri, et al., 2005, *Stem Cells Dev* 14:204-212; Ryan, et al., 2005, *J Inflamm (Lond)* 2:8, each of which is incorporated by reference herein in its entirety). These stem cells also have the ability to non-specifically modulate the immune response through the suppression of dendritic cell maturation and antigen presenting abilities (Beyth, et al., 2005, *Blood* 105:2214-2219; Aggarwal, et al., 2005, *Blood* 105:1815-1822, each of which is incorporated by reference herein in its entirety). Functional induction of allogeneic T cell apoptosis was also demonstrated using freshly isolated, irradiated, or long-term cultured mesenchymal stem cells (Plumas, et al., 2005, *Leukemia* 19:1597-1604, which is incorporated by reference herein in its entirety). Others have also demonstrated that mesenchymal stem cells have the ability to preferentially induce expansion of antigen specific T regulatory cells with the CD4+CD25+ phenotype (Maccario, et al., 2005, *Haematologica* 90:516-525, which is incorporated by reference herein in its entirety). Supporting the potential clinical utility of such cells, it was previously demonstrated that administration of mesenchymal stem cells inhibits antigen specific T cell responses in the murine model of multiple sclerosis, experimental autoimmune encephalomyelitis, leading to prevention and/or regression of pathology (Zappia, et al., 2005, *Blood* 106:1755-1761, which is incorporated by reference herein in its entirety). Safety of infusing mesenchymal stem cells was illustrated in studies administering $1-2.2\times10^6$ cells/kg in order to enhance engraftment of autologous bone marrow cell. No adverse events were associated with infusion, although level of engraftment remained to be analyzed in randomized trials (Koc, et al., 2000, *J Clin Oncol* 18:307-316, which is incorporated by reference herein in its entirety). In a matched pair analysis study, it was demonstrated that in vitro expanded mesenchymal stem cells reduced both acute and chronic graft versus host disease in the allogeneic bone marrow transplant setting. Clinical administration of mesenchymal stem cells was reported in a patient suffering severe, grade IV graft versus host disease in the liver and gut subsequent to bone marrow transplant. Administration of 2×10$^6$ cells/kg on day 73 after bone marrow transplant lead to a long term remission of graft versus host disease, which was maintained at the time of publication, 1 year subsequent to administration of the mesenchymal stem cells (Le Blanc, et al., 2004, *Lancet* 363:1439-1441, which is incorporated by reference herein in its entirety). A feasibility study in 46 patients receiving mesenchymal cells prior to transplant revealed a favorable safety profile and is encouraging further dose finding studies (Lazarus, et al., 2005, *Biol Blood Marrow Transplant* 11:389-398, which is incorporated by reference herein in its entirety). Unfortunately, mesenchymal cell expansion is relatively slow and in many situations is not practical for widespread clinical use. The development of novel methods of expanding stem cell populations, as for example the methods thought in the present invention, are likely to increase use of this therapeutically promising cell population.

There is evidence that embryonic stem cells are also capable of inducing immunological tolerance. Indeed, coculture of alloreactive T cells with embryonic T cells demonstrated an antigen-specific inhibitory effect (Li, et al., 2004, *Stem Cells* 22:448-456, which is incorporated by reference herein in its entirety). Data is still preliminary in this area, and the problem of embryonic stem cells inducing teratomas currently precludes their use for this indication. An alternative method of immune modulation using embryonic stem cells is the generation of defined immunological cells that can be used directly, or tailored to possess specific desired properties through modification of culture conditions or gene manipulation. For example, it was demonstrated that the murine model of multiple sclerosis, experimental autoimmune encephalomyelitis can be successfully treated with dendritic cells generated from embryonic stem cell cultures that have been manipulated to present the MOG autoantigen in the presence of TRAIL, a molecule known to induce T cell apoptosis (Hirata, et al., 2005, *J Immunol* 174:1888-1897, which is incorporated by reference herein in its entirety). Generation of such tailor-made immunological cells would greatly expand the clinical armamentarium of immunotherapy, however, this is limited by the currently lack of methodologies for expanding stem cells in a GMP/GTP compliant and feasible manner.

One of the main therapeutic uses for stem cells is in the area of regenerative medicine. The concept of regenerative medicine is to restore or enhance the ability of tissues to self-organize and heal themselves following endogenous or exogenous injury. Although examples of the use of stem cells for tissue regeneration are almost limitless, several are overviewed below. This should not be taken as an exhaustive literature review, but rather a general discussion for example purposes in order to stimulate one skilled in the art to further investigate this field.

Bone marrow stem cells have been extensively investigated for repair of myocardial tissue subsequent to infarction. Early studies by Orlic demonstrated that administration of GFP c-kit+, lineage–, bone marrow into ligation induced myocardial infarct area resulted in regeneration of myocardial and endothelial tissue by the donor cells (Orlic, et al., 2001, *Nature* 410:701-705, which is incorporated by reference herein in its entirety). Subsequent studies have used mesenchymal bone marrow cells treated with the DNA methyltransferase inhibitor 5-aza-cytidine to not only transdifferentiate into myocardial tissue, but also to improve left ventricular ejection fraction and inhibit cardiac remodeling (Tomita, et al., 1999. *Circulation* 100:II247-256, which is incorporated by reference herein in its entirety). Importantly, similar experiments were performed in porcine models of infarction, also indicating improvement in cardiac function (Tomita, et al., 2002, *J Thorac Cardiovasc Surg* 123:1132-1140, which is incorporated by reference herein in its entirety). Accordingly, clinical experiments were performed administering autologous bone marrow cells directly into the myocardium during coronary bypass grafting. In a series of experiments initiated in 1999, 5 patients treated had no adverse effects, with objective vascularization enhancement in the area of stem cell administration as detected by nuclear imaging (Hamano, et al., 2001, *Jpn Circ J* 65:845-847, which is incorporated by reference herein in its entirety). A subsequent study administering AC133 purified bone marrow stem cells into the infarct area in 12 patient during bypass grafting demonstrated a marked improvement in left ventricular ejection fraction, a decreased rate of remodeling, and improved perfusion (Stamm, et al., 2004, *Thorac Cardiovasc Surg* 52:152-158, which is incorporated by reference herein in its entirety). Administration of stem cells into coronary circulation or directly into the myocardium has also been performed both in the angina setting, as well as subsequent to cardiac infarct in order to enhance angiogenesis, and prevent remodeling, respectively. In patients with end stage angina, administration of autologous bone marrow cells using the NOGA catheter system in 14 patients resulted in improved ejection fraction from a baseline of 20% to 29% (P=0.003) and a reduction in end-systolic volume (P=0.03) in the treated patients. Furthermore, electromechanical mapping revealed significant mechanical improvement of the injected segments (P<0.0005) at 4 months after treatment (Perin, et al., 2003, *Circulation* 107:2294-2302, which is incorporated by reference herein in its entirety). Improvements were also notably maintained in the same patient population at 1-year follow-up (Perin, E., 2004, *Int J Cardiol* 95 Suppl 1:S45-46, which is incorporated by reference herein in its entirety). Transcoronary administration of bone marrow cells in patients post-myocardial infarction induced an improvement at 6 months in regional and global LV function, increased thickness of the infarcted wall, and showed a reduction in myocardial remodeling as determined by a decrease in the end-systolic volume (Fernandez-Aviles, et al., 2004, *Circ Res* 95:742-748, which is incorporated by reference herein in its entirety). In another study, patients post myocardial infarction were transplanted with autologous bone marrow cells via a balloon catheter placed into the infarct-related artery during balloon dilatation (percutaneous transluminal coronary angioplasty), resulting in decreased infarct size, improved wall motion score, and a decrease in ventricular remodeling (Strauer, et al., 2002, *Circulation* 106:1913-1918, which is incorporated by reference herein in its entirety). Randomized trials are currently underway using autologous bone marrow stem cells for increasing cardiac function post myocardial infarction although results are still controversial and inconclusive (Assmus, et al., 2002, *Circulation* 106:3009-3017; Cleland, et al., 2006, *Eur J Heart Fail* 8:105-110, each of which is incorporated by reference herein in its entirety). In addition to bone marrow hematopoietic cells, other types of stem cells have been utilized for improvement in myocardial activity, perfusion, and decreasing ventricular remodeling. These include mesenchymal stem cells (Chen, et al., 2004, *Chin Med J (Engl)* 117:1443-1448, which is incorporated by reference herein in its entirety), endothelial stem cells (Aoki, et al., 2005, *J Am Coll Cardiol* 45:1574-1579, which is incorporated by reference herein in its entirety), and skeletal myoblasts (Ye, et al., 2006. *Exp Biol*

Med (Maywood) 231:8-19, which is incorporated by reference herein in its entirety). A limiting factor in presently used cellular therapies for myocardial dysfunction is the lack of ability to induce transdifferentiation of the stem cells into the desired cardiac tissue in a directed manner. Additionally, methods do not exist for expanding sufficient numbers of semi-differentiated progenitor stem cells that possess a high proclivity for repairing the heart. This drawback is in part due to lack of proper culture mediums for expansion of such unique cell populations. The current invention addresses this issue.

The importance of stem cells inducing regeneration of other organ systems has been shown in a variety of settings. In a pathological setting, it was reported that bone marrow derived stem cells are the precursors of stomach epithelial tissue in *Helicobacter pylori* infected mice that progresses to the develop stomach cancer (Houghton, et al., 2004, *Science* 306:1568-1571, which is incorporated by reference herein in its entirety). In a therapeutic setting, administration of Green Fluorescent Protein (GFP) bone marrow stem cells into rats with ethanol-induced ulcers resulted in generation of GFP expressing, cytokeratin-positive epithelial cells and vimentin-positive interstitial cells, contributing to a decreased pathology in the stem cell recipients (Komori, et al., 2005, *J Gastroenterol* 40:591-599, which is incorporated by reference herein in its entirety). The human bone marrow derived Flk1(+)/CD31(−)/CD34(−) cell population was reported to transdifferentiated into a variety of tissues, including stomach epithelium when injected into non-obese diabetic, severe combined immunodeficient (NOD-SCID) mice, thus suggesting human stem cells also possess such transdifferentiation ability (Fang, et al., 2003, *J Hematother Stem Cell Res* 12:603-613, which is incorporated by reference herein in its entirety). Stomach-homing capacity to injured tissue of human stem cells was demonstrated human mesenchymal stem cells infused systemically in NOD-SCID mice that received radiation to the abdominal area. This resulted in a specific rise in stem cell engraftment exclusively to the irradiated areas (Francois, et al., Local irradiation induces not only homing of human Mesenchymal Stem Cells (hMSC) at exposed sites but promotes their widespread engraftment to multiple organs: A study of their quantitative distribution following irradiation damages. Stem Cells, e-published on Dec. 8, 2005, which is incorporated by reference herein in its entirety) It is anticipated that since stem cells can selectively home to the injured stomach area, addition of factors to allow expansion once already homed into the injured tissue will increase therapeutic efficacy of stem cell therapies. The invention teaches methods of expanding cells that have already homed to an injured tissue.

The use of stem cells has also been applied to liver disease. It is known that partial hepatectomy leads to mobilization of an AC133+ stem cell population in clinical situations (Gehling, et al., 2005, *J Hepatol* 43:845-853, which is incorporated by reference herein in its entirety). Furthermore, studies using carbon tetrachloride induced liver injury have demonstrated a therapeutic effect of bone marrow flk-1+ cell infusion (Fang, et al., 2004, *Transplantation* 78:83-88, which is incorporated by reference herein in its entirety). It is believed that liver damage induces expression of several chemokines, including stromal derived factor-1 (SDF-1) which attracts stem cells into the damaged areas (Hatch, et al., 2002, *Cloning Stem Cells* 4:339-351, which is incorporated by reference herein in its entirety). Therapeutic mobilization of endogenous stem cells using granulocyte colony stimulating factor (G-CSF) has also demonstrated protective effects in liver injury models (Quintana-Bustamante, et al., 2006, *Hepatology* 43:108-116, which is incorporated by reference herein in its entirety). It is anticipated that since stem cells can selectively home to the injured hepatic area, addition of factors to allow expansion once already homed into the injured tissue will increase therapeutic efficacy of stem cell therapies. The invention teaches methods of expanding cells that have already homed to an injured tissue.

Stem cells have also been useful for treatment of neurological deficiencies in a variety of situations. Administration of fetal stem cells in the form of mesenchphalic tissue into the striatal area of Parkinson's disease (PD) patients have demonstrated that grafted dopaminergic neurons can reinnervate the striatum, restore regulated dopamine release and movement-related frontal cortical activation, and result in observable clinical benefit (Lindvall, et al., 2004, *NeuroRx* 1:382-393, which is incorporated by reference herein in its entirety). Patients suffering from stroke have also been treated by implantation of autologous mesenchymal stem cells into the middle cerebral arterial territory. Improvements were seen in some functional indexes such as the Barth's score (Bang, et al., 2005, *Ann Neurol* 57:874-882; Rabinovich, et al., 2005, *Bull Exp Biol Med* 139:126-128, each of which is incorporated by reference herein in its entirety). A wide variety of neurological indications are currently under investigation for amenability to stem cell therapy (Kulbatski, et al., 2005, *Curr Drug Targets* 6:111-126; Zhu, et al., 2005, *Curr Drug Targets* 6:97-110, each of which is incorporated by reference herein in its entirety). Unfortunately, ethical issues associated with the use of fetal tissue, as well as inability to define the activities and functions of neurally injected stem cells hampers progress in the field. Development of novel culture and expansion methodologies for stem cell applications is therefore an important area of issue.

SUMMARY OF THE INVENTION

In one aspect of the invention, a method of preparing live placenta conditioned media (LPCM) is disclosed. Said LPCM is prepared through contacting a media suitable for maintaining cellular viability in vitro with at least a portion of a placenta under conditions allowing transfer of molecules from said placenta into said media.

In one embodiment of the invention, the placenta may be a hemochorial, epitheliochorial, or endotheliochorial. In a preferred embodiment the placenta is hemochorial. The placenta can be collected subsequent to vaginal delivery or collected pre-term by cesarean section, depending on biological properties desired. The placenta can be brought in contact with said media through immersing said placenta in media, through co-culture of placental tissue in said media, or through perfusion of said media through the placenta in a discontinuous or continuous manner. The placenta can be in its entirety or dissected into individual units or cellular components. Contact between said placenta and media can be achieved through a filter apparatus whereby molecules of a specific size are allowed to permeate through said filter, whereas molecules of a larger size are excluded.

In one embodiment of the invention, a full term placenta obtained from a vaginal delivery is exanguinated and washed in saline using an anticoagulant. LPCM is produced through perfusing said placenta in a continuous circuit using a peristaltic pump preset for a volume of perfusion sufficient to maintain placental integrity. The peristaltic pump can cause flow of the perfusion solution in a pulsatile or non-pulsatile manner. In another embodiment, other means of passaging media through the placenta may be employed such as a syringe filled with media.

In some embodiments, LPCM is collected from the perfused solution at a time-point sufficient to allow transfer of molecules with desired biological properties from the placenta to the media. Temperature, pH, intravasular pressure, flow rate, oxygen and carbon dioxide concentrations, as well as osmolarity of the perfusion solution may be monitored and adjusting accordingly to achieve desired properties of the LPCM. Attachment of the perfusion system to said placenta may be accomplished by perfusion of media through the umbilical artery(s) and collection through the umbilical vein and/or through the exterior of the placental structure through diffusion. Subsections of the placenta may be perfused individually for example the truncal branch of the chorionic artery supplying a selected cotyledon and the associated vein may be perfused on the fetal side, or selective maternal circulation as described in studies perfusing placenta for detection of maternal to fetal drug transfer (Forestier, et al., 2001, *Am J Obstet Gynecol* 185:178-181, which is incorporated by reference herein in its entirety). Media chosen for perfusion may be an isotonic solution, a buffered solution, or a solution capable of functioning as a growth medium. The growth media can contain, if desired, a growth factor, combinations of growth factors, or substantial nutrient content allowing for increased viability of the placenta to be perfused. Additional agents may be introduced into the perfusion solution, including agents to prevent clotting, maintain pH, or to maintain a desired osmolarity or oxygen content. For example heparin, buffers, zwitterions, or artificial/natural oxygen carriers can be added. Agents inhibiting apoptosis such as caspase inhibitors can also be incorporated in order to preserve certain functions of placental tissue. The contacting step between the growth media and the placenta can occur, for example, at a temperature range of from about 32° C. to about 40° C.

Another embodiment of the current invention involves modification of placental conditions through either upregulating or inhibiting oxygen content in the placenta in order to modify growth factor release.

In another aspect of the invention, a method for the expansion or growth of stem cells is provided, by incubating at least a portion of a placenta in a growth medium to condition the medium, and contacting at least one stem cell with the growth medium hemochorial, epitheliochorial, or endotheliochorial. In a preferred embodiment the placenta is hemochorial. The placenta may be collected subsequent to vaginal delivery or collected pre-term by cesarean section, depending on biological properties desired. In a preferred embodiment the placenta is hemochorial. The stem cell can be, for example, a mesenchymal stem cell, or a fetal stem cell. The stem cells can be derived from an umbilical cord, such as, for example, from umbilical cord blood. The stem cells can be derived from an umbilical cord that expresses a $CD34^+$ cell marker. The umbilical cord stem cells and said placenta can be derived, for example, from a mammal, such as a human. The growth medium can also contain, if desired, a growth factor, combinations of growth factors, or substantial nutrient content allowing for increased viability of the stem cells. The incubating step can occur, for example, at a temperature range of from about 32° C. to about 40° C. The placenta can be removed from the medium prior to the contacting step, if desired. The placenta can either be perfused with the medium or it may be cultured in the medium at conditions that allow for release of growth factors.

Further embodiments include a method of optimizing growth factor production from said placenta conditioned media through the use of filters that separate compositions based on electrical charge, size or ability to elute from an adsorbent. Numerous techniques are known in the art for purification of growth factors and concentration of said agents. For some particular uses the placental conditioned medium will be sufficient for use in its current format and will not require concentration, however numerous other uses may. In order to identify and standardize placental conditioned media, one embodiment of the invention is the concept of "units of activity" for quantification of LPCM activity in which 1 Unit of LPCM is sufficient to stimulate a biological activity sought to a certain degree. Depending on use, this can be stimulation of a standardized cell culture to proliferate by a certain percentage, in other desired uses the Unit may designate the amount needed to inhibit differentiation a specified culture condition by a defined percentage.

The use of placental conditioned media as a combination to known cocktails is also an embodiment of the invention. In addition to actual soluble components already used in stem cell culture medias, LPCM can be used to synergize with plate-bound stimulators, as well as antibodies and other methods known in the art to induce cycling in a stem cell. These are well known in the art and include contact-dependent factors including heparan sulfate-bound cytokines such as members of the fibroblast growth factor family (de Haan, et al., 2003, *Dev Cell* 4:241-251, which is incorporated by reference herein in its entirety), and ligands of VLA-4 and -5 (Jung, et al., 2005, *Cytokine* 32:155-162, which is incorporated by reference herein in its entirety), as well as antibodies to TGF-β (Imbert, et al., 1998, *Exp Hematol* 26:374-381, which is incorporated by reference herein in its entirety).

In some embodiments of the invention, a method for the expansion or growth of stem cells is provided, by incubating at least a portion of a placenta in a growth medium to condition the medium, and contacting at least one stem cell with the growth medium. The stem cell can be a) A totipotent cell such as an embryonic stem cell, an extra-embryonic stem cell, a cloned stem cell, a parthenogenesis derived cell; b) A pluripotent cell such as a hematopoietic stem cell, an adipose derived stem cell, a mesenchymal stem cell, a cord blood stem cell, a placentally derived stem cell, an exfoliated tooth derived stem cells, a hair follicle stem cell or a neural stem cell; or c) A tissue specific progenitor cell such as a precursor cell for the neuronal, hepatic, nephrogenic, adipogenic, osteoblastic, osteoclastic, alveolar, cardiac, intestinal, or endothelial lineage. The incubating step can occur, for example, at a temperature range of from about 32° C. to about 40° C. The placenta can be removed from the medium prior to the contacting step, if desired.

An additional embodiment of the invention teaches addition of certain factors to the perfusion mixture used to perfuse said placenta such that the placenta generates endogenous growth factors, which are capable of either stimulating stem cell expansion on their own, or having synergy with other growth factors.

In additional embodiments of the invention, a method for the expansion or growth of umbilical cord stem cells is provided, by contacting at least one stem cell with a liquid that has been incubated with at least a portion of a placenta. The contacting step can occur, for example, after the incubating step. The contacting step can occur simultaneously with the incubating step. The incubating step can occur, for example from about 1 second to about 3 weeks. The incubating step can occur, for example, from about 24 hours to about 10 days. The contacting step can occur, for example, from about 1 second to about 3 weeks. The contacting step can occur, for example, from about 24 hours to about 10 days. The stem cells can be stored, for example, prior to the contacting step using a freezing process.

Another embodiment is the use of LPCM alone or in combination with other approaches expanding cells that have been generated for a specific phenotype, and are at risk of losing the phenotype that was artificially endowed upon them. Specifically, it is known that administration of a certain compounds to stem cells induces differentiation into certain lineage-specific progenitors. For example, addition of thrombopoietin alone or in combination with interleukin 11 to early hematopoietic stem cells will promote the preferential production of megakaryocytic progenitors. One embodiment of the current invention is the ability of LPCM, alone or in combination with other growth factors and/or culture conditions to maintain and expand the new phenotype of the differentiated progenitor cell without stimulation of terminal differentiation. For example, subsequent to increasing the numbers of megakaryocytic progenitors in a stem cell culture, LPCM may be added to maintain said progenitors and expand their numbers.

Another embodiment of the invention relates to generation and expansion of cells expressing a desired phenotype through cytoplasmic reprogramming wherein the cytoplasmic extracts of a cell with a desired property are introduced into the cytoplasm of a recipient cell with the aim of introducing the properties of the donor cell into the recipient cell (Hakelien, et al., 2002, *Nat Biotechnol* 20:460-466, which is incorporated by reference herein in its entirety). Such reprogramming can be useful for generating autologous stem cells from non-stem cells of a patient by introduction of cytoplasm from the stem cell of an allogeneic patient. One drawback of this technology has been the limited ability to expand the reprogrammed cell after introduction of cytoplasm without differentiation. Accordingly, the invention teaches the use of LPCM either alone or in combination with other factors in order to induce expansion of the reprogrammed cell.

An aspect of the invention is the use of LPCM as an adjuvant to currently used stem cell feeder-free mixtures that are currently limited by ability to achieve desired expansion of stem cells of the phenotype sought.

Another embodiment of the invention is a stimulator of proliferation of totipotent stem cells such as such as human embryonic stem cells characterized by expression of markers such as SSEA-4, GCTM-2 antigen, TRA 1-60, Cripto, gastrin-releasing peptide (GRP) receptor, podocalyxin-like protein (PODXL), or human telomerase reverse transcriptase (hTERT). The LPCM can be used as a stimulator of proliferation alone or as an additive to media known to be useful for culturing said cells. An example of such a tissue culture media is Dulbecco's modified Eagle's medium (DMEM). In an ideal embodiment LPCM is used in such a manner and under such conditions so as to alleviate the need for serum or feeder cells in the culture of human embryonic stem cells.

Another embodiment of the invention is a stimulator of proliferation of totipotent stem cells generated by cloning through the use of nuclear transfer technologies. The LPCM can be used as a stimulator of proliferation alone or as an additive to media known to be useful for culturing said cells.

Another embodiment of the invention is a stimulator of proliferation of totipotent stem cells such as such as human oocyte producing stem cells characterized by expression of markers such Vasa, Oct-4, Dazl, Stella, Fragilis, Nobox, c-Kit and Sca-1. The LPCM can be used as a stimulator of proliferation alone or as an additive to media known to be useful for culturing said cells.

Another embodiment of the invention is a stimulator of proliferation of totipotent stem cells such as such as parthenogenetically generated stem cells characterized by expression of markers such Oct-4, alkaline phosphatase, telomerase, SSEA-4, TRA 1-60 and TRA 1-81. The LPCM can be used as a stimulator of proliferation alone or as an additive to media known to be useful for culturing said cells.

Another embodiment of the invention is a stimulator of proliferation of totipotent stem cells such as such as spermatogonial stem cells reprogrammed to pluripotent germline stem cells characterized by expression of markers such Oct-4, Nanog, Dppa5 and Rex1. The LPCM can be used as a stimulator of proliferation alone or as an additive to media known to be useful for culturing said cells.

Another embodiment of the invention is the generation of totipotent stem cells through the steps of: a) treating bone marrow cells with LPCM in combination with sera from a female in a period of the menstrual cycle associated with upregulation of oocyte stem cell markers in the bone marrow; b) addition of a calcium flux inducing agent to activate said oocyte precursors into the process of parthenogenesis; c) purifying cells expressing embryonic stem cell markers such as SSEA-4, TRA 1-60 or TRA 1-81; and d) expanding said cells in a culture media containing LPCM alone or in combination with agents and conditions known to induce totipotent stem cell proliferation.

Another embodiment of the invention is a stimulator of proliferation of pluripotent stem cells such as hematopoietic stem cells characterized by markers such as Stem Cell Antigen (SCA+), lineage negative (lin-), c-kit+, CD34+, CD38-, CD33-. The LPCM can be used as a stimulator of proliferation alone or as an additive to media known to be useful for culturing said cells.

Another embodiment of the invention is a stimulator of proliferation of pluripotent stem cells such as mesenchymal stem cells characterized by markers such as LFA-3, ICAM-1, PECAM-1, P-selectin, L-selectin, CD49b/CD29, CD49c/CD29, CD49d/CD29, CD61, CD18, CD29, 6-19, thrombomodulin, telomerase, CD10, CD13, STRO-1, STRO-2, VCAM-1, CD146, THY-1. The LPCM can be used as a stimulator of proliferation alone or as an additive to media known to be useful for culturing said cells.

Another embodiment of the invention is a stimulator of proliferation of pluripotent stem cells such as placentally derived multipotent cells characterized by markers such as Oct-4, Rex-1, CD9, CD13, CD29, CD44, CD166, CD90, CD105, SH-3, SH-4, TRA-1-60, TRA-1-81, SSEA-4 and Sox-2. The LPCM can be used as a stimulator of proliferation alone or as an additive to media known to be useful for culturing said cells.

Another embodiment of the invention is a stimulator of proliferation of pluripotent stem cells such as adipose-derived stem cells characterized by markers such as CD13, CD29, CD44, CD63, CD73, CD90, CD166, Aldehyde dehydrogenase (ALDH), and ABCG2. The LPCM can be used as a stimulator of proliferation alone or as an additive to media known to be useful for culturing said cells.

Another embodiment of the invention is a stimulator of proliferation of pluripotent stem cells such as cord blood stem cells characterized by markers such as CD34, c-kit, and CXCR-4. The LPCM can be used as a stimulator of proliferation alone or as an additive to media known to be useful for culturing said cells.

Another embodiment of the invention is a stimulator of proliferation of pluripotent stem cells such as deciduous tooth stem cells characterized by markers such as STRO-1, CD146 (MUC18), alkaline phosphatase, MEPE, and bFGF. The LPCM can be used as a stimulator of proliferation alone or as an additive to media known to be useful for culturing said cells.

Another embodiment of the invention is a stimulator of proliferation of progenitor stem cells such as neural stem cells characterized by markers such as RC-2, 3CB2, BLB, Sox-2hh, GLAST, Pax 6, nesting, Muashi-1, and prominin. The LPCM can be used as a stimulator of proliferation alone or as an additive to media known to be useful for culturing said cells.

Another embodiment of the invention is a stimulator of proliferation of progenitor stem cells such as a stomach epithelial stem cell characterized by markers such as Musashi-1, c-hairy-1 and HES-5. The LPCM can be used as a stimulator of proliferation alone or as an additive to media known to be useful for culturing said cells.

Another embodiment of the invention is a stimulator of proliferation of progenitor stem cells such as a skeletal muscle stem cell characterized by markers such as desmin positive, SCA-1+, CD45− and possessing a side population profile on flow cytometry by dye exclusion (Challen, et al., 2006, Stem Cells 24:3-12, which is incorporated by reference herein in its entirety). The LPCM can be used as a stimulator of proliferation alone or as an additive to media known to be useful for culturing said cells.

Another embodiment of the invention is a stimulator of proliferation of progenitor stem cells such as a mammary gland stem cell characterized by markers such as SCA-1 positive, CD45− and keratin-6. The LPCM can be used as a stimulator of proliferation alone or as an additive to media known to be useful for culturing said cells.

Another embodiment of the invention is a stimulator of proliferation of progenitor stem cells such as a dermal stem cell characterized by markers such as SCA-1 positive, CD34+, CD45− and positive for alpha6-integrin, beta1-integrin, keratin 14, and keratin 19. The LPCM can be used as a stimulator of proliferation alone or as an additive to media known to be useful for culturing said cells.

Another embodiment of the invention is a stimulator of proliferation of progenitor stem cells such as a myocardial stem cell characterized by markers such as SCA-1 positive, c-kit positive, and possessing a side population profile on flow cytometry by dye exclusion (Challen, supra). The LPCM can be used as a stimulator of proliferation alone or as an additive to media known to be useful for culturing said cells.

Another embodiment of the invention is a stimulator of proliferation of progenitor stem cells such as a mesangial stem cell characterized by markers such as SCA-1 positive, c-kit positive, and possessing a side population profile on flow cytometry by dye exclusion (Challen, supra). The LPCM can be used as a stimulator of proliferation alone or as an additive to media known to be useful for culturing said cells.

Another embodiment of the invention is a stimulator of proliferation of progenitor stem cells such as a hepatic oval stem cell characterized by markers such as SCA-1 positive, c-kit positive, and CD34 positive. The LPCM can be used as a stimulator of proliferation alone or as an additive to media known to be useful for culturing said cells.

Another embodiment of the invention is a stimulator of proliferation of progenitor stem cells such as a pancreatic stem cell characterized by markers such as nestin, CK-8, CK-18, Isl-1, Pdx-1, Pax-4, and Ngn-3. The LPCM can be used as a stimulator of proliferation alone or as an additive to media known to be useful for culturing said cells.

Another embodiment of the invention is the administration of LPCM into a subject in order to stimulate the proliferation and expansion of endogenous stem cells that have been activated as part of the healing process after injury.

Another embodiment of the invention is the administration of LPCM into a subject in order to stimulate the proliferation and expansion of endogenous stem cells that have been mobilized from the bone marrow to a target organ as a result of injury.

Another embodiment of the invention a treatment for a degenerative condition by the application of a combination of LPCM with known therapies in order to enhance the beneficial effects of known therapies.

Another embodiment of the invention an adjuvant to therapies, interventions, or accidents that destroy or inactivate stem cells with the goal of accelerating stem cell reconstitution. Examples of situations where accidental stem cell destruction occurs would include a nuclear event.

Within the embodiments of the invention is the use of LPCM, or extracts thereof, to enhance proliferation of stem cells within a living organism. Administration of such media can be performed systemically, or in a localized environment Clinical situations where administration of such placentally conditioned media is desirable can include conditions where an increase in the number of stem cells is sought due to disease or senescence of endogenous stem cells. Specific aspects of this include conditions in which a higher number and/or more rapid recovery of stem cells is needed after a medical procedure. One such situation would be post bone marrow transplant where expansion of hematopoietic cells is desirable in order for the patient not to succumb to bacterial or viral infections. Specifically, LPCM may be used in conjunction with a growth factor that stimulates preferential differentiation of the bone marrow stem cell into the granulocytic and/or monocytic lineage such as G-CSM or GM-C SF. Such an expansion of granulocytic and monocytic precursors would be useful in enhancing immunological defenses subsequent to a bone marrow transplant. If clinically desirable the number of endogenous dendritic cells can also be expanded through administration of cytokines such as flt-3L in combination with LPCM. Accordingly, this invention provides methods and compositions that can be administered to a patient having undergone a bone marrow transplant that will enhance proliferation and bone marrow take.

Yet another embodiment is supporting the expansion of endogenous stem cells after a injury has occurred and the endogenous stem cells are mobilized or begin to differentiated, but do not do so at high enough levels to stimulate a beneficial response. Said endogenous stem cells can be present in pancreatic tissue, liver tissue, smooth muscle tissue, striated muscle tissue, cardiac muscle tissue, bone tissue, bone marrow tissue, bone spongy tissue, cartilage tissue, liver tissue, pancreas tissue, pancreatic ductal tissue, spleen tissue, thymus tissue, Peyer's patch tissue, lymph nodes tissue, thyroid tissue, epidermis tissue, dermis tissue, subcutaneous tissue, heart tissue, lung tissue, vascular tissue, endothelial tissue, blood cells, bladder tissue, kidney tissue, digestive tract tissue, esophagus tissue, stomach tissue, small intestine tissue, large intestine tissue, adipose tissue, uterus tissue, eye tissue, lung tissue, testicular tissue, ovarian tissue, prostate tissue, connective tissue, endocrine tissue, and mesentery tissue.

Another embodiment is the use of LPCM as a source of angiogenic/endothelial cell migration/proliferation factor for the stimulation of angiogenesis in a patient in need thereof. The amount of angiogenic stimulatory activity can be increased in the LPCM through perfusing the placenta under conditions of hypoxia or near hypoxia. LPCM can be used alone or in combination with known angiogenesis promoters. The angiogenic promoters can include proteins such as FGF-1, FGF-2, VEGF, transcription factors such as the Hypoxia Inducible Factor (HIF-1), or small molecule stimulators of endothelial proliferation such as an artificial agonist of an angiogenically relevant receptor. Proteins may be administered locally to the patient through means such as intramuscular injection, or systemically. Additionally, genes encoding angiogenically stimulatory growth factors may be delivered in the form of naked plasmid DNA, adenoviruses, or other means known to one skilled in the art. Additionally, LPCM can be administered in combination with stem cells capable of inducing angiogenesis for augmenting the ability of said stem cells. Said stem cells may be derived from a variety of tissue, such as adipose, cord blood, placenta, bone marrow, peripheral blood, or growth factor/chemotherapy mobilized peripheral blood. In addition, the cells to be administered can be allogeneic or autologous. For some purposes, cells can be matched according to the Human Leukocyte Antigen haplotype.

Medical conditions amenable to such treatments may include peripheral limb ischemia, myocardial angina, mesenteric ischemia, ischemia reperfusion injury and general circulatory disorders.

Another embodiment of the invention is the use of LPCM alone or in combination with growth factors to promote healing. In one aspect, scarless healing is promoted through concentration of factors such as TGF-b within the LPCM through selective purification of LCMP fractions containing this TGF-b or similar proteins involved in tissue repair without promotion of fibrosis. Alternatively, LPCM can be administered in conjunction with antibodies or inhibitors to fibrosis promoting cytokines or factors.

Another embodiment of the invention is the use of LPCM for cosmetic purposes in order to enhance skin rejuvenation. LPCM can be administered in a variety of dermatologically applicable formulations, either alone or in combination with other factors capable of restoring certain properties to skin. Additionally, LPCM can be used in combination with agents capable of de-differentiating skin such as histone deacetylase inhibitors, DNA methylase inhibitors, or other epigenetically acting compounds in order to allow expansion of local dermal precursor cells. Such stem cell expansion can be tailored to allow formation of skin with appearances desirable to the common population.

Another embodiment of the invention is a treatment for diabetes by administering LPCM in combination with factors capable of inducing islet regeneration. These factors can be, for example, soluble proteins, membrane bound proteins or intracellular acting transcription factors. For example, it is known that administration into mice combinations of GLP-1, EGF and gastrin leads to regeneration of islets or islet-like cells that are functionally effective in models like NOD or streptozocin induced diabetes (Bonner-Weir, et al., 2005, *Nat Biotechnol* 23:857-861, which is incorporated by reference herein in its entirety). When these experiments were translated to humans, only a marginal therapeutic effect was seen, and this was observed only in a small subset of patients (von Herrath, M., 2005, *Curr Opin Investig Drugs* 6:1037-1042, which is incorporated by reference herein in its entirety). The invention teaches that use of placental conditioned media can be added to cultures of differentiating islets in vitro to expand numbers, but can also be added to a patient in vivo in order to amplify the relatively minute effect that the hormones are evoking in terms of differentiation induction.

Another embodiment of the invention a treatment for multiple sclerosis utilizing LPCM for expanding neuronal progenitors and subsequent reintroduction of said progenitors into a host in need thereof. Alternatively, LPCM can be administered into patients suffering from multiple sclerosis in combination with agents capable of inhibiting the autoimmune process Synergy in therapeutic effects is anticipated through the concurrent induction of tissue healing and immune system repair.

Another embodiment of the invention is the treatment of an immunological disorder, such as an autoimmune disorder, by extracting hematopoietic cells from an autologous patient, treating the cells with LPCM and/or other combinations of stem cell expanding compounds, ablating the immune system of the patient, and subsequent reintroduction of stem cells into the host for reconstitution. LPCM may be subsequently provided to the host in order to accelerate reconstitution of hematopoiesis. Autoimmune diseases treatable by these procedures include, but are not limited to, Type 1 diabetes, multiple sclerosis, rheumatoid arthritis, systemic sclerosis, Hashimoto's thyroiditis, myasthenia gravis, scleroderma, systemic lupus erythromatosis, graft versus host disease, and the like.

Another embodiment of the invention in relation to autoimmune diseases, and also transplant rejection, involves the use of LPCM for expansion of antigen-specific and/or non-specific immune regulatory cells for use in controlling a pathological immune response. It is known that cells such as Th2 cells (Christen, et al., 2004, *Immunol Res* 30:309-325), Th3 cells (Prud'homme, et al., 2000, *J Autoimmun* 14:23-42), TR1 cells (Bacchetta, et al., 2005, *Autoimmun Rev* 4:491-496), CD4+CD25+FoxP3+ cells (Bluestone, et al., 2005, *Curr Opin Immunol* 17:638-642), and CD3+ double negative cells (Zhang, et al., 2001, *J Mol Med* 79:419-427), each of which is incorporated by reference herein in its entirety, are capable of suppressing immune responses in an antigen specific manner, whereas NKT cells (Van Kaer, L., 2005, *Nat Rev Immunol* 5:31-42), myeloid suppressor cells (Serafini, et al., 2004, *Cancer Immunol Immunother* 53:64-72), M2 cells (Rauh, et al., 2004, *Biochem Soc Trans* 32:785-788), and immature dendritic cells (Ichim, et al., 2003, *Transpl Immunol* 11:295-306), each of which is incorporated by reference herein in its entirety, are capable of suppressing immune responses in an antigen non-specific manner. Despite the fact that all of these cells have potential therapeutic value, their clinical development has been hindered by lack of methodology for expansion ex vivo and maintenance of function subsequent to expansion. The invention teaches the use of LPCM for use in ex vivo culture and expansion of immune regulatory cells derived from a patient in need thereof. LPCM may be used either alone or in combination with factors known to be involved in the development of said cells. Alternatively, immune regulatory cells can be generated through the use of stem cells through exposure to factors involved in their development and LPCM being added to enhance proliferation of said cells without loss of function.

Another embodiment of the invention is a treatment for stroke comprising induction of in vitro differentiation of neural precursor cells using a conditioning regimen, expansion of said cells using LPCM, and reintroduction of said cells into a patient in need thereof. Alternatively, in vivo differentiation of endogenous neural cells can be accomplished by administration of polypeptides and proteins known in the art. Subsequent or concurrent with this differentiation, administration of LPCM may be given in order to expand neural cells.

Another embodiment is the use of LPCM in storage and transportation of stem cells in order to maintain viability, mobility and stem cell function. LPCM may be used alone or added to a variety of agents known in the art to allow transportation of stem cells. This is particularly important in situations of bone marrow stem cell transportation in which cell freezing and thawing is not performed in numerous situations. The ability to adequately store stem cells during transportation would allow for tissue extraction at separate physical locations from the stem cell processing facility.

Another embodiment of the invention is the use of LPCM alone or in combination with other factors for maintaining stem cells in a totipotent, pluripotent, or progenitor state while allowing sufficient viability and proliferation ex vivo so as to be useful for gene therapy. Said gene therapy can be used for introducing new genes into a host in need thereof. Genes may be introduced by a wide range of approaches known in the art including adenoviral, adeno-associated, retroviral, lentiviral, Kunjin virus, or HSV vectors, as well as electroporation and Sleeping Beauty transposons. Additionally, gene therapy can include selectively silencing genes through the use of antisense, ribozyme or RNA interference technologies.

In some embodiments of the invention, a method for the expansion or growth of stem cells without substantially inducing differentiation is provided, by incubating at least a portion of a placenta in a growth medium to condition the medium, and contacting at least one stem cell with the growth medium. The at least one stem cell can be, for example, totipotent, capable of differentiating into cells of all histological types of the body. The totipotent stem cell can be selected, for example, from an embryonic stem cell, an extra-embryonic stem cell, a cloned stem cell, a parthenogenesis derived cell. The embryonic stem cell can express, for example, one or more of the following markers: stage-specific embryonic antigens (SSEA) 3, SSEA 4, Tra-1-60 and Tra-1-81, Oct-3/4, Cripto, gastrin-releasing peptide (GRP) receptor, podocalyxin-like protein (PODXL), or human telomerase reverse transcriptase (hTERT). The hematopoietic stem cells can express, for example, one or more of the following markers: CD34, c-kit, and the multidrug resistance transport protein (ABCG2). The adipose-derived stem cells can express, for example, one or more of the following markers: CD13, CD29, CD44, CD63, CD73, CD90, CD166, Aldehyde dehydrogenase (ALDH), and ABCG2. The mesenchymal stem cells can express, for example, one or more of the following markers: STRO-1, CD105, CD54, CD106, HLA-I markers, vimentin, ASMA, collagen-1, and fibronectin, but not HLA-DR, CD117, and hemopoietic cell markers. The cord blood stem cells can express, for example, one or more of the following markers: CD34, c-kit, and CXCR-4. The placental stem cells can express, for example, one or more of the following markers: Oct-4, Rex-1, CD9, CD13, CD29, CD44, CD166, CD90, CD105, SH-3, SH-4, TRA-1-60, TRA-1-81 SSEA-4 and Sox-2. The exfoliated deciduous tooth stem cells can express, for example, one or more of the following markers: STRO-1, CD146 (MUC18), alkaline phosphatase, MEPE, and bFGF. The neural stem cell can be characterized, for example, by expression of RC-2, 3CB2, BLB, Sox-2hh, GLAST, Pax 6, nesting, Muashi-1, and prominin. The at least one stem cell can be pluripotent, capable of differentiating into numerous cells of the body, but not all. The pluripotent stem cell can be selected from hematopoietic stem cells, adipose stem cells, mesenchymal stem cells, cord blood stem cells, placental stem cells, exfoliated teeth derived stem cells, hair follicle stem cells or neural stem cells. The at least one stem cell can be a progenitor cell, capable of differentiating into a restricted tissue type. The progenitor stem cell can be selected from, for example, neuronal, hepatic, nephrogenic, adipogenic, osteoblastic, osteoclastic, alveolar, cardiac, intestinal, endothelial progenitor cells.

In some embodiments of the present invention, a method for the expansion or growth of stem cells without substantially inducing differentiation is provided, by incubating at least a portion of a placenta in a growth medium to condition the medium, and contacting at least one stem cell with the growth medium. The placenta can be derived from a mammal. The placenta can be derived from a human. The placenta can be derived preterm. The placenta can be derived at term. The placenta can be perfused for a period of time with a cell culture media. The cell culture media can be supplemented, for example, with a single or a plurality of growth factors. The growth factors can be selected from, for example, a WNT signaling agonist, TGF-b, bFGF, IL-6, SCF, BMP-2, thrombopoietin, EPO, IGF-1, IL-11, IL-5, Flt-3/Flk-2 ligand, fibronectin, LIF, HGF, NFG, angiopoietin-like 2 and 3, G-CSF, GM-CSF, Tpo, Shh, Wnt-3a, Kirre, or a mixture thereof. The media can be capable of maintaining viability of a substantial portion of the placental tissue during the perfusion process. The media can be selected, for example, from Roswell Park Memorial Institute (RPMI-1640), Dublecco's Modified Essential Media (DMEM), Eagle's Modified Essential Media (EMEM), Optimem, and Iscove's Media. The source of serum can be added to the media. The concentration of serum in the media can be approximately between 0.1% to 25%. The concentration of serum in the media can be approximately 10%. The serum can be selected from adult human serum, fetal human serum, fetal calf serum and umbilical cord blood serum. The contacting step can occur after the incubating step. The contacting step can occur simultaneously with the incubating step. The incubating step can occur from about 1 second to about 3 weeks. The incubating step can occur from about 24 hours to about 10 days. The contacting step can occur from about 1 second to about 3 weeks. The contacting step can occur from about 24 hours to about 10 days. The placenta can be, for example, a hemochorial, epitheliochorial, or endotheliochorial placenta. The perfusion can be accomplished, for example, through the use of a perfusion apparatus cannulated to blood vessels connected to the placental body. The perfusion apparatus can allow for control of intravasular pressure, oxygen content, carbon dioxide content, pH, and flow rate of the perfused media flowing through the placental blood vessels. The intravasular pressure of the perfusate can be maintained, for example, at 30-80 Hg. The intravasular pressure of the perfusate can be maintained at 60 Hg.

In an additional embodiment of the present invention, a stem cell with the preserved ability to proliferate, but having a block in differentiation state is provided, which can be induced by culturing in media conditioned by perfusion through a live placenta. The stem cell can be selected, for example, from a totipotent stem cell, a pluripotent stem cell, and a progenitor stem cell. The stem cell can be maintained in contact with the conditioned media, for example, for a period of less than 1 second, 2 hours, 12 hours, 24 hours, 72 hours, or 3 weeks or more. The stem cell can be maintained in contact with the conditioned media in a living organism. The contact between the conditioned media and the stem cell can be prolonged by formulating the conditioned media in a slow release delivery system. The stem cell can be initially cultured in contact with the placentally conditioned media for a period of time, subsequently to which it can be cultured in a second culture with a different concentration of placentally conditioned media and an identical or variable mix of cytokines. The stem cell can be initially cultured for 48 hours in a concentration of 20-100% placentally conditioned media, whereas in subsequent cultures it can be maintained in a concentration of 0-50% conditioned media. The stem cell can be maintained in a cell culture media that can be supplemented with at least one growth factor selected from the group consisting of WNT signaling agonist, TGF-b, bFGF, IL-6, SCF, BMP-2, thrombopoietin, EPO, IGF-1, IL-11, IL-5, Flt-3/Flk-2 ligand, fibronectin, LIF, HGF, NFG, angiopoietin-like 2 and 3, G-CSF, GM-CSF, Tpo, Shh, Wnt-3a, Kirre, and a mixture thereof. The stem cell can be maintained in a 50% by volume placentally conditioned DMEM media with the following growth factors also in DMEM media: IL-3 (about 20 ng/ml), IL-6 (about 250 ng/ml), SCF (about 10 ng/ml), TPO (about 250 ng/ml), flt-3L (about 100 ng/ml). The stem cell can be maintained in the presence of an agent selected from one or more of the following: an inhibitor of GSK-3, an inhibitor of histone deacetylase activity, and inhibitor of DNA methyltransferase activity. The stem cell can be rejuvenated by at fusion with a more primitive stem cell, transfer of cytoplasm from more primitive stem cells, and/or transfer of karyoplastic extracts from a more primitive stem cell.

In an additional embodiment of the present invention, a method of treating degenerative diseases through administration of a composition of matter derived from media conditioned by a live placenta is provided. The degenerative disease effects a tissue selected from the group consisting of: smooth muscle tissue, striated muscle tissue, cardiac muscle tissue, bone tissue, bone spongy tissue, nervous system tissue, cartilage tissue, pancreatic ductal tissue, spleen tissue, thymus tissue, tonsil tissue, Peyer's patch tissue, lymph nodes tissue, thyroid tissue, epidermal tissue, dermal tissue, subcutaneous tissue, heart tissue, lung tissue, vascular tissue, endothelial tissue, blood cells, bladder tissue, kidney tissue, digestive tract tissue, esophagus tissue, stomach tissue, small intestine tissue, large intestine tissue, adipose tissue, uterus tissue, eye tissue, lung tissue, testicular tissue, ovarian tissue, prostate tissue, connective tissue, endocrine tissue, and mesentery tissue. The placenta conditioned media can be administered in combination with an agent capable of inducing stem cell expansion. The placenta conditioned media can be administered in combination with an agent capable of inducing stem cell differentiation into cells of the tissue in need of repair. The agent capable of inducing stem cell expansion can be selected from TPO, SCF, IL-1, IL-3, IL-7, flt-3L, G-CSF, GM-CSF, Epo, FGF-1, FGF-2, FGF-4, FGF-20, VEGF, activin-A, IGF, EGF, NGF, LIF, PDGF, and a member of the bone morphogenic protein family. The agent capable of inducing stem cell differentiation can be selected from HGF, cardiotrophin, BDNF, VEGF, FGF1, FGF2, FGF4, and FGF 20. The placental conditioned media can be concentrated to a sufficient extent to allow systemic administration while retaining biological effects. The placental conditioned media can be calibrated for specific Units of Activity based on a desired biological property. The biological activity can be the ability to stimulate proliferation of a defined culture of CD34 stem cells by 50%. The placentally conditioned media can be administered according to biomarkers of stem cell activity in the patient in need of treatment. The biomarker may be either an indicator of disease activity, or an indicator of stem cell regeneration. The clinically applicable agent that possesses stem cell mobilizing activity can be administered in conjunction with the placentally conditioned media and/or the stem cell proliferation inducing growth factor, and/or the inducer of stem cell differentation. The stem cell mobilizing agent may be an antibody, a small molecule, or a protein. The stem cell mobilizing agent can be an antibody to CXCR-4. The stem cell mobilizing agent can be either a small molecular inhibitor of CXCR-4, or a statin. The stem cell mobilizing agent can be, for example, a cytotoxic chemotherapy known to mobilize stem cells, or can be a growth factor such as G-CSF. The dedifferentiation agent can be used for expanding the differentiation potential of the stem cells. The dedifferentiation agent can be, for example, an inhibitor of the enzyme GSK-3, and inhibitor of the histone deacetylase family of enzymes, or an inhibitor of DNA methyltransferase activity. The dedifferentiation agents can be, for example, trichostatin A, valproic acid, buphenyl, or 5-azacytidine.

In an additional embodiment of the present invention, a method of treating degenerative diseases is provided, by administering a differentiating agent to selectively expand a population of pluripotent or progenitor cells, while concurrently administering live placental conditioned media in order to induce proliferation of the committed stem cell.

In an additional embodiment of the present invention, a method of expanding stem cells that have been therapeutically reprogrammed is provided, by contacting the cells with media that has been conditioned by a live placenta. The therapeutic reprogramming can be accomplished by introduction into the target cell to be reprogrammed agents capable of acting at the epigenetic level to modify the cellular transcriptosome into a desired phenotype. The target cell can be fused with another cell of a more primitive state of differentiation. The cell can be temporarily permeabilized and cytoplasmic and/or karyoplasmic extracts are introduced into the cell from another cell of a more primitive state of differentiation.

In an additional embodiment of the present invention, a method of accelerating hematopoietic recovery in a patient in need thereof is provided, by administering placentally conditioned media. In some embodiments, the patient has been treated with chemotherapy, and/or radiotherapy with the scope of either ablating or diminishing the immune system. The patient can have been treated, for example, with chemotherapy, and/or radiotherapy with the scope of eradicating or ameliorating a malignancy. The patient can have been induced into a state of reduced hematopoiesis as a result of chemical or radiation poisoning. In some embodiments, the patient was not administered a cellular graft to enhance recovery of the hematopoietic system. The patient can have been administered either cord blood derived, peripheral blood derived, or bone marrow derived hematopoietic stem cells or progenitors thereof. The patient can be administered placentally conditioned media intravenously at a concentration sufficient to accelerate recovery of early hematopoietic progenitors. The patient can be administered placentally conditioned media at a concentration of 10-500 Units of placentally conditioned media per kilogram per day, the Units based on a logarithmic scale in which 1 Unit can be sufficient to stimulated proliferation of a defined cell culture of CD34+ cells by 100% compared to control media. The 1 Unit can be defined on a logarithmic scale as the amount of placentally conditioned media needed to stimulate proliferation of a 200 µL culture of $5\times10^3$ human cord blood isolated CD34+. The patient can be treated intravenously, or through other means, with placental conditioned media for a period of time needed to obtain a granulocyte count of $500/mm^3$. The patient can be treated intravenously, or through other means, with placental conditioned media for a period of time between 7 days to 15 days. The growth factor can be concurrently given with the administration of placentally conditioned media. The growth factor can be selected from G-CSF, pegylated G-CSF, TPO, IL-11, GM-CSF, or flt-3L.

In an additional embodiment of the present invention, a method of treating patient with tissue ischemia through induction of endothelial stem cell expansion using placentally conditioned media is provided. The ischemia can be present, for example, in at least one tissue selected from smooth muscle tissue, striated muscle tissue, cardiac muscle tissue, bone tissue, bone spongy tissue, nervous system tissue, cartilage tissue, pancreatic ductal tissue, spleen tissue, thymus tissue, tonsil tissue, Peyer's patch tissue, lymph nodes tissue, thyroid tissue, epidermis tissue, dermis tissue, subcutaneous tissue, heart tissue, lung tissue, vascular tissue, endothelial tissue, blood cells, bladder tissue, kidney tissue, digestive tract tissue, esophagus tissue, stomach tissue, small intestine tissue, large intestine tissue, adipose tissue, uterus tissue, eye tissue, lung tissue, testicular tissue, ovarian tissue, prostate tissue, connective tissue, endocrine tissue, and mesentery tissue. The ischemia can be presenting, for example, as advanced angina. The placentally conditioned media can be concentrated and administered into the ischemic myocardium using the minithoracotomy procedure. The placentally conditioned media can be concentrated and administered into the ischemic myocardium using the NOGA electromagnetic mapping and injection system. The placentally conditioned media can be concentrated and administered into the ischemic myocardial area using a balloon catheter. A secondary agent can be added that can be capable of inducing proliferation of differentiated and undifferentiated endothelial cells. The secondary agent can be, for example, a nucleic acid, a protein, or a small molecule. The secondary agent can be, for example, plasmid DNA encoding a polypeptide selected from HIF-1, VEGF, FGF1, FGF2, FGF4, FGF20, and angiopoietin. The secondary agent can be, for example, VEGF, FGF1, FGF2, FGF4, FGF20, or angiopoietin. An exogenous or endogenous source of stem cells can be delivered into the ischemic area. The exogenous stem cells can be autologous or allogenenic mesenchymal, adipose, endothelial, bone marrow, mobilized peripheral blood, umbilical, or artificially reprogrammed stem cells. The endogenous stem cells can be mobilized with a mobilization agent. The patient suffering from ischemia can be a victim of Critical Limb Ischemia. The patient can be administered a combination of placentally conditioned media intramuscularly in the area of ischemia as detected by angiography. The autologous or allogenenic mesenchymal, adipose, endothelial, bone marrow, mobilized peripheral blood, umbilical, or artificially reprogrammed stem cells can be injected with the placentally conditioned media in a localized environment intramuscularly. The autologous lymphocytes can be injected with the stem cell source in order to synergize with the placentally conditioned media and the injected stem cells. In some embodiments, the patient has suffered from a cerebral ischemia. The patient can be treated immediately after the ischemia episode or in a period of time subsequently.

In an additional embodiment of the present invention, a method of culturing a placenta in its original 3-dimensional structure is provided, in such a manner as to reproduce the in vivo environment in which it resides in the pregnant woman, thus retaining capability of generation and secretion of growth factors and proteins that maintain the fetal regenerative capacity. The method involves acquiring a placenta under sterile conditions, cannulating blood vessels of the placenta in order to allow proper perfusion in circumstances similar to as if the placenta was performing its in vivo functions, perfusing the placenta with a nutrient mix in a buffer that would mimic physiological conditions, maintaining a temperature and physical environment similar to that found in the pregnant woman's body, and imitating conditions of flow, pH, oxygenation, and pressure similar to that found in the body. The perfusion of both the maternal and fetal circulatory components of the placenta can be performed. A nutrient mixture can be used that possesses similar nutrient requirements as the fetal and maternal circulation, respectively. A temperature of 37° C. can be maintained during the perfusion process. The pH can be monitored, for example, by the perfusion apparatus in a real-time basis, and adjusted using adequate quantities of acids, bases, or buffers. The oxygen content can be maintained similar to that found in the fetal and maternal circulatory contribution to the placenta. The oxygen content may be increased, for example, through the use of adding natural or artificial oxygen carriers to the perfusion solution. An oxygenator may be attached to the perfusion apparatus, in conjunction with, or separately, from an oxygen sensor, the combination being used to adjust in real-time oxygen content. The osmolality can be maintained, for example, through the use of known means such as addition of albumin or colloids to the perfusion solution.

In an additional embodiment of the present invention, a method of producing a cosmetic for topical use in rejuvenating aged skin is provided, by concentrating placentally conditioned media, quantifying and standardizing biological effect of the media, and formulating the media in a carrier solution that is suitable for transdermal delivery. The media can be, for example, a physiological buffer, a media capable of maintaining cellular viability, or a media enriched in nutrients and mimicking the content of the maternal/fetal circulation. The media can be selected from DMEM, RPMI, and saline USP. The media can contain, for example, an anticoagulant at sufficient quantities to inhibit clotting during placental perfusion. The quantification can be based on the ability of placentally conditioned media to induce proliferation of dermal stem cells. A moisturizing agent can be added to the cosmetic preparation. The carrier can contain nutrients replenishing to the skin. The carrier can contain, for example, a single or a plurality of anti-oxidant compounds.

DETAILED DESCRIPTION OF THE INVENTION

The present invention provides a method of increasing the growth of stem cells. The method involves mixing the stem cells with a growth medium that has been conditioned by an incubation with placental tissue.

The invention disclosed herein teaches compositions and methods relating to using the placenta as a potent source of stem cell growth factors for the expansion of stem cells either in vitro or in vivo. Additionally, the ability to almost block cells at a specific stage of differentiation and allow their expansion through administration of the compositions described herein, and extrapolated upon by one skilled in the art will be very important for the development of stem cell therapeutics as a discipline and field of medicine.

Furthermore, there is a need for agents which, in addition to increasing the rate of stem cell proliferation, also maintain the stem cells in an undifferentiated state. This becomes particularly apparent when one considers that, in general, stem cells reside in unique physiological niches, and while growing cells within mimics of such niches has been performed, the mimics of the stem cell niche are often unusable in clinical situations. An example of this is the fact that early hematopoietic stem cells require feeder cell lines to be expanded in high quantities, or the fact that optimal growth of embryonic stem cells is still primarily achieved using murine feeders. The current invention teaches methods and compositions for recreating conditions similar to stem cell niches using approaches that are translatable into the clinical situation.

General Information Regarding Stem Cell Expansion Techniques

As shown in the description herein, it becomes apparent that methods of extracting, expanding and identifying specific phenotypes of said stem cells is important for clinical implementation. For example, bone marrow is commonly used as a source of therapeutic stem cells for myocardial disease, angina, and hematopoietic cell transplant. However, bone marrow in general contains a wide number of different stem cells in addition to the standard, well known, hematopoietic CD34+ stem cell. CD34− hematopoietic stem cells (Bhatia, et al., 1998, *Nat Med* 4:1038-1045), oocyte generating stem cells (Johnson, et al., 2005, *Cell* 122:303-315), mesenchymal stem cells (Dazzi, et al. The role of mesenchymal stem cells in haemopoiesis. *Blood Rev.*, e-published on Dec. 15, 2005), and myogenic precursor cells (Bhagavati, et al., 2004, *Biochem Biophys Res Commun* 318:119-124), each of which is incorporated by reference herein in its entirety, have all been found in the bone marrow, in addition to T cells, B cells, and relatively high levels of CD4+CD25+T regulatory cells (Zeng, et al., 2004, *Transplantation* 77:S9-S11, which is incorporated by reference herein in its entirety). Given the heterogeneity of bone marrow as a starting material for stem cell therapy, it is apparent that understanding of particular cell populations, as well as ability to isolate and expand them, would substantially advance the field of stem cell therapeutics.

Accordingly, whether a stem cell population is derived from adult or embryonic sources, the stem cells can be grown in a culture medium to increase the population of a heterogeneous mixture of cells, or a purified cell population. The cell growth can be slow, however, and the cells can differentiate to unwanted cell types during the culture period. Thus, methods of improving the growth rate of stem cells, in general, and defined stem cell populations in particular, will be useful for advancing the clinical use of stem cells. Accordingly, what is needed is novel methods of increasing the rate of expansion or growth of the stem cells when grown in culture.

Several methods of growing stem cells outside of the body have been developed and are known in the art. Originally, the majority of work in the area of stem cell growth and expansion was performed in the hematopoietic system using bone marrow cells. The ability of either freshly isolated or cultured bone marrow cells to form colonies on methylcellulose or agar was used as an output. Colonies of hematopoietic stem cells were typically designated based on cellular morphology into the broad subsets of colony forming unit-erythroid (CFU-E), burst forming unit-erythroid (BFU-E), colony forming unit-granulocytic monocytic (CFU-GM), colony forming unit-monocytic (CFU-M), colony forming unit-granulocytic (CFU-G), colony forming unit-granulocytic, erthrocytic, monocytic, megakarocytic (CFU-E). Identification of colonies was usually performed under light microscopy and allowed quantification of relatively mature progenitor cells (Jacobs, et al., 1979. *Exp Hematol* 7:177-182, which is incorporated by reference herein in its entirety). Addition of biologically derived supernatants to the semi-solid media was performed in order to search for agents that preferentially enhanced formation of certain types of colonies. For example, addition of leukocyte or monocyte supernatant was shown to stimulate preferential growth of CFU-GM colonies, indicating that this factor possesses similar activity in vivo (Galbraith, et al., 1979, *Can Med Assoc J* 121:172-178, which is incorporated by reference herein in its entirety). In influence of in vivo situations on the ability of bone marrow to form CFU-E was used in the identification of erythropoietin biological activities (Peschle, et al., 1977, *Br J Haematol* 37:345-352, which is incorporated by reference herein in its entirety). It is generally regarded that the longer it takes to form colonies in the semisolid media, and the larger the size and cellular constitution of the colonies, the earlier in ontogeny the stem cell that initiated the colony is. Unfortunately, multilineage stem cells capable of producing other hematopoietic cells such as lymphocytes could not be identified using such semi-solid culture assays. The long term culture (LTC) system was developed to detect earlier progenitor cells then can be detected by semisolid assays. LTC assays involve the use of pre-established layers of stromal cells (ie bone marrow fibroblasts or transformed cytokine-secreting cell lines) that provide signals for viability and proliferation of the earlier progenitors. It is believed that the cell initiating the LTC, the LTC initiating cell (LTC-IC) is an early precursor cell capable of reconstituting a lethally irradiated mouse (Ploemacher, et al., 1991, *Blood* 78:2527-2533, which is incorporated by reference herein in its entirety). The LTC system has been established as a method of assessing various growth factors and combinations thereof for ability to expand hematopoietic stem cells in vitro. The expansion activities of proliferin-2 (Choong, et al., 2003, *FEBS Lett* 550:155-162), protease inhibitors (Isgro, et al., 2005, *AIDS Res Hum Retroviruses* 21:51-57), PDGF (Su, et al., 2002, *Br J Haematol* 117:735-746), each of which is incorporated by reference herein in its entirety, as well as numerous other factors was demonstrated using the LTC system. More direct evidence of hematopoietic stem cell activity is derived from in vivo model systems. The original identification of the colony forming unit-spleen (CFU-S) was made by Till and McCulloch in 1964 through the observation that transfer of bone marrow cells into lethally irradiated mice gave rise to colonies comprising of multi-lineage phenotypes (Till, et al., 1964, *Proc Nall Acad Sci USA* 51:29-36, which is incorporated by reference herein in its entirety). These cells demonstrated the ability for serial transplantation and reconstitution of hematopoiesis, thereby suggesting a stem cell-like characteristic (Siminovitch, et al., 1964, *J Cell Physiol* 64:23-31, which is incorporated by reference herein in its entirety). Modern day implementation of this technique is the SCID Repopulating Cell (SRC) assay whereby putative human hematopoietic stem cells are transferred to an irradiated NOD-SCID recipient and ability to reconstitute full hematopoiesis is observed (Larochelle, et al., 1996, *Nat Med* 2:1329-1337, which is incorporated by reference herein in its entirety). This is currently considered the standard assay for hematopoietic stem cells, and it is currently believed that 1 in 3 million bone marrow mononuclear cells have this ability (Wang, et al., 1997, *Blood* 89:3919-3924, which is incorporated by reference herein in its entirety). Assessment of SRC numbers is routinely performed during evaluation of stem cell expansion protocols (Kawada, et al., 1999, *Exp Hematol* 27:904-915; Yamaguchi, et al., 2001, *Exp Hematol* 29:174-182, each of which is incorporated by reference herein in its entirety).

The development of stem cell expansion techniques began with work aimed at increasing the number of colonies formed on semisolid media. Early experiments used a variety of uncharacterized sera and conditioned media. For example, trophoblast cell line conditioned media (Ferrero, et al., 1987, *Cancer Res* 47:6413-6417), xenogeneic stromal cell conditioned media (Li, et al., 1987, *Exp Hematol* 15:373-381), supernatants from tumor cells (Tweardy, et al., 1987, *Ann NY Acad Sci* 511:30-38), and healthy lymphocytes were used (Iscove, et al., 1971, *Blood* 37:1-5), each of which is incorporated by reference herein in its entirety. Work was also performed towards designing serum free systems, using ingredients such as human transferrin and bovine insulin (Taketazu, et al., 1984, *Cancer Res* 44:531-535, which is incorporated by reference herein in its entirety). The realization that stem cells assessed by the semisolid CFU assays are already differentiated, led to the use of stromal feeder cells to allow expansion of LTC-IC as described above. The specific advantage of the LTC system is that hematopoietic stem cells could be expanded without concurrent differentiation. The initial systems of LTC required the use of murine feeder (stromal) cells since human lines had certain disadvantages in terms of hematopoietic promoting activity (Petzer, et al., 1996, *Proc Natl Acad Sci USA* 93:1470-1474, which is incorporated by reference herein in its entirety). Numerous drawbacks existed to the use of murine feeder cell lines to maintain stem cell viability and proliferative potential. Due to this, an effort was made to overcome difficulties in growth of human derived feeder cells, and a variety of such cells have been developed (Thalmeier, et al., 1994, *Blood* 83:1799-1807; Kohler, et al., 1999, *Stem Cells* 17:19-24; Guo, et al., 2000, *Zhongguo Shi Yan Xue Ye Xue Za Zhi* 8:93-96; De Angeli, et al., 2004, *Int J Mol Med* 13:363-371, each of which is incorporated by reference herein in its entirety).

In terms of hematopoiesis, the role of the feeder cells is to mimic the natural hematopoietic environment in the bone marrow in which the hematopoietic stem cells reside in an area populated by fibroblasts and other mesenchymal cells which present growth factors directly and indirectly to the hematopoietic stem cell. In this regard, the invention disclosed seeks to mimic the situation of stem cell generation in general, and hematopoiesis specifically in some embodiments, by taking advantage of a new method of utilizing placental tissue. It is known that the placenta contains endogenous multipotent stem cells characterized by markers such as SSEA-4, TRA-1-61, TRA-1-80, CD105, endoglin, SH-2, SH-3, and SH-4 (Yen, et al., 2005, *Stem Cells* 23:3-9), as well as mesenchymal (Wulf, et al., 2004, *Tissue Eng* 10:1136-1147) and hematopoietic stem cells (Gekas, et al., 2005, *Dev Cell* 8:365-375, Fauza, D., 2004, *Best Pract Res Clin Obstet Gynaecol* 18:877-891), each of which is incorporated by reference herein in its entirety. Furthermore, the use of cord blood cells from placentas is an established clinical treatment for a wide variety of diseases and medical situations (Chao, et al., 2004, *Hematology (Am Soc Hematol Educ Program)*:354-371, which is incorporated by reference herein in its entirety). The interest in the placenta is due not only to the finding of such cells, but the possibility that the presence of these cells has some biological ramifications. The presence of a variety of different stem cell tissues in the placenta at high concentrations suggest that certain factors are present within it that are hospitable for stem cell growth in a natural milieu. Indeed, it was recently published that during development, the placenta acts as a depot for hematopoiesis, much in a similar way how the liver performs this function during fetal development (Ottersbach, et al., 2005, *Dev Cell* 8:377-387; Li, L., 2005, *Dev Cell* 8:297-298, each of which is incorporated by reference herein in its entirety).

The ease of harvesting placental material, as well as ability to maintain its viability as a three dimensional structure, allows for various manipulations and extraction of trophic factors from it. The placenta is the only stem cell bearing organ that can be continually perfused while maintaining structural integrity in a clinically feasible manner. The use of factors derived from placenta have potent applications not only for ex vivo expansion of cells for therapeutic purposes, but also for in vivo expansion of stem cells. It is known in a wide variety of disease conditions that stem cells are mobilized from various pools and go into the source of injury (Francois, supra; Wojakowski, et al., 2005, *Folia Histochem Cytobiol* 43:229-232; Claps, et al., 2005, *Curr Neurovasc Res* 2:319-329; Abbott, et al., 2004, *Circulation* 110:3300-3305, each of which is incorporated by reference herein in its entirety). Unfortunately, unlike the amphibians who are capable of limb regeneration through production of a high concentration of stem cells (blastema) (Brockes, et al., 2005, *Science* 310:1919-1923, which is incorporated by reference herein in its entirety), human stem cells only make what is considered to be a relatively therapeutic "spark" in absence of exogenous support growth factor support. Furthermore, it is known that higher concentrations of progenitor cells are associated with scarless healing in certain mouse strains (Davis, et al., 2005, *Blood Cells Mol Dis* 34:17-25, which is incorporated by reference herein in its entirety), and possibly account for this phenomena in human fetuses (Howell, L. J., 1994, *Nurs Clin North Am* 29:681-694, which is incorporated by reference herein in its entirety). Therefore, many investigators have attempted to use a variety of growth factors in order to induce stem cell mobilization and then expansion of the mobilized stem cells in order to evoke the healing processes, or to transform the "spark" into an "explosion." Although this was demonstrated by mobilization of stem cells using G-CSF in patients with myocardial infarction, the results have accomplished only moderate success (Powell, et al., 2005, *Arterioscler Thromb Vasc Biol* 25:296-301; Belenkov Iu, et al., 2003, *Kardiologiia* 43:7-12, each of which is incorporated by reference herein in its entirety). Accordingly, there is a need for a multifactorial stimulator of stem cells that is active both in vivo as well as in vitro.

Preparation of Stem Cells to be Expanded

The term "stem cell" generally refers to any cells that have the ability to divide for indefinite periods of time and to give rise to specialized cells. Within the definition of "stem cell" we include but not limit, to the following: a) totipotent cells such as an embryonic stem cell, an extra-embryonic stem cell, a cloned stem cell, a parthenogenesis derived cell, a cell reprogrammed to possess totipotent properties, or a primordial germ cell; b) Pluripotent cell such as a hematopoietic stem cell, an adipose derived stem cell, a mesenchymal stem cell, a cord blood stem cell, a placentally derived stem cell, an exfoliated tooth derived stem cells, a hair follicle stem cell or a neural stem cell; and c) A tissue specific progenitor cell such as a precursor cell for the neuronal, hepatic, nephrogenic, adipogenic, osteoblastic, osteoclastic, alveolar, cardiac, intestinal, or endothelial lineage. The cells can be derived, for example, from tissues such as pancreatic tissue, liver tissue, smooth muscle tissue, striated muscle tissue, cardiac muscle tissue, bone tissue, bone marrow tissue, bone spongy tissue, cartilage tissue, liver tissue, pancreas tissue, pancreatic ductal tissue, spleen tissue, thymus tissue, Peyer's patch tissue, lymph nodes tissue, thyroid tissue, epidermis tissue, dermis tissue, subcutaneous tissue, heart tissue, lung tissue, vascular tissue, endothelial tissue, blood cells, bladder tissue, kidney tissue, digestive tract tissue, esophagus tissue, stomach tissue, small intestine tissue, large intestine tissue, adipose tissue, uterus tissue, eye tissue, lung tissue, testicular tissue, ovarian tissue, prostate tissue, connective tissue, endocrine tissue, and mesentery tissue.

The stem cells to be expanded can be isolated from any organ of any mammalian organism, by any means known to one of skill in the art. The stem cells can be derived from embryonic or adult tissue. One of skill of the art can determine how to isolate the stem cells from the particular organ or tissue of interest, using methods known in the art. In a preferred embodiment, the stem cells are isolated from umbilical cord blood. Example 2 describes a typical method that can be used to isolate stem cells from umbilical cord blood. In this example, the stem cell marker CD34 is used to enrich the stem cell population, using antibodies to CD34.

The stem cell populations can also be enriched using antibodies to other stem cell surface markers. Such markers include, but are not limited to, FLK-1, AC133, CD34, c-kit, CXCR-4, Oct-4, Rex-1, CD9, CD13, CD29, CD44, CD166, CD90, CD105, SH-3, SH-4, TRA-1-60, TRA-1-81, SSEA-4, Sox-2, and the like. One of skill in the art will be able to determine the specific cell marker useful for isolating stem cells from the desired tissue.

One of skill in the art will be able to determine a suitable growth medium for initial preparation of stem cells. Commonly used growth media for stem cells includes, but is not limited to, Iscove's modified Dulbecco's Media (IMDM) media, DMEM, KO-DMEM, DMEM/F12, RPMI 1640 medium, McCoy's 5A medium, minimum essential medium alpha medium (α-MEM), F-12K nutrient mixture medium (Kaighn's modification, F-12K), X-vivo 20, Stemline, CC100, H2000, Stemspan, MCDB 131 Medium, Basal Media Eagle (BME), Glasgow Minimum Essential Media, Modified Eagle Medium (MEM), Opti-MEM I Reduced Serum Media, Waymouth's MB 752/1 Media, Williams Media E, Medium NCTC-109, neuroplasma medium, BGJb Medium, Brinster's BMOC-3 Medium, CMRL Medium, CO2-Independent Medium, Leibovitz's L-15 Media, and the like.

If desired, other components, such as growth factors, can be added as desired. Exemplary growth factors and other components that can be added include but are not limited to thrombopoietin (TPO), stem cell factor (SCF), IL-1, IL-3, IL-7, flt-3 ligand (flt-3L), G-CSF, GM-CSF, Epo, FGF-1, FGF-2, FGF-4, FGF-20, IGF, EGF, NGF, LIF, PDGF, bone morphogenic proteins (BMP), activin-A, VEGF, forskolin, glucocorticords, and the like. Furthermore, the media can contain either serum such as fetal calf, horse, or human serum, or more preferably, serum substitution components. Numerous agents have been introduced into media to alleviate the need for serum. For example, serum substitutes have included bovine serum albumin (BSA), insulin, 2-mercaptoethanol and transferrin (TF).

The stem cells can then be stored for a desired period of time, if needed. Stem cell storage methods are known to those of skill in the art. Typically, the stem cells are treated to a cryoprotection process, then stored frozen until needed. Cryopreservation requires attention be paid to three main concepts, these are: 1) The cryoprotective agent, 2) the control of the freezing rate, and 3) The temperature at which the cells will be stored at. Cryoprotective agents are well known to one skilled in the are and can include but are not limited to dimethyl sulfoxide (DMSO), glycerol, polyvinylpyrrolidine, polyethylene glycol, albumin, dextran, sucrose, ethylene glycol, i-erythritol, D-ribitol, D-mannitol, D-sorbitol, i-inositol, D-lactose, or choline chloride as described in U.S. Pat. No. 6,461,645, which is incorporated by reference herein in its entirety. A method for cryopreservation of stem cells that is preferred by some skilled artisans is DMSO at a concentration not being immediately cytotoxic to cells, under conditions which allow it to freely permeate the cell whose freezing is desired and to protect intracellular organelles by combining with water and prevent cellular damage induced from ice crystal formation. Addition of plasma at concentrations between 20-25% by volume can augment the protective effect of DMSO. After addition of DMSO, cells can be kept at temperatures below 4° C., in order to prevent DMSO mediated damage. Methods of actually inducing the cells in a state of suspended animation involve utilization of various cooling protocols. While cell type, freezing reagent, and concentration of cells are important variables in determining methods of cooling, it is generally accepted that a controlled, steady rate of cooling is optimal. There are numerous devices and apparatuses known in the field that are capable of reducing temperatures of cells for optimal cryopreservations. One such apparatus is the Thermo Electro Cryomed Freezer™ manufactured by Thermo Electron Corporation. Cells can also be frozen in CryoCyte™ containers as made by Baxter. One example of cryopreservation is as follows: $2 \times 10^6$ CD34 cells/ml are isolated from cord blood using the Isolex System™ as per manufacturer's instructions (Baxter). Cells can be incubated in DMEM media with 10% DMSO and 20% plasma. Cooling is generally performed at 1° C./minute from 0 to −80° C. When cells are needed for use, they can be thawed rapidly in a water bath maintained at 37° C. water bath and chilled immediately upon thawing. The cells can then be rapidly washed, using, for example, either a buffer solution, or a solution containing a growth factor. Purified cells can then be used for expansion with LPCM. A database of stored cell information (such as donor, cell origination types, cell markers, etc.) can also be prepared, if desired. Further, the stem cells can be obtained, if desired, from a library of publicly available stored stem cells, including the National Institute of Health or American Type Culture Collection.

The stem cells can be purified prior to contacting the LPCM by methods known in the art, using, for example, antibody technology such as panning of cells, through the use of fluorescence activated cell sorting (FACS) methods, or magnet activated cell sorting methods such as that MACS apparatus, to isolate cells having the desired stem cell markers, or to remove unwanted, contaminating cell types having unwanted cell markers prior to contacting with LPCM. Other methods of stem cell purification or concentration can include the use of techniques such as counterflow centrifugal elutriation, equilibrium density centrifugation, velocity sedimentation at unit gravity, immune rosetting and immune adherence, T lymphocyte depletion. Examples of stem cell markers that can be useful in purification include, but are not limited to, FLK-1, AC133, CD34, c-kit, CXCR-4, Oct-4, Rex-1, CD9, CD13, CD29, CD44, CD166, CD90, CD105, SH-3, SH-4, TRA-1-60, TRA-1-81, SSEA-4, Sox-2, and the like. Examples of cell surface markers that can be used as markers of contaminating, unwanted cell types depends on the stem cell phenotype sought. For example, if collection of pluripotent hematopoietic cells is desired, contaminating cells will possess markers of commitment to the differentiated hematopoietic cells such as CD38 or CD33. Additionally, non-hematopoietic cell contamination would be detected by lack of CD45 expression. If selection of stromal mesenchymal cells is desired, then contaminating cells would be detected by expression of hematopoietic markers such as CD45. Additionally, stem cells can be purified based on properties such as size, density, adherence to certain substrates, or ability to efflux certain dyes such as Hoechst 33342 or Rhodamine 123.

The stem cells can be genetically modified at any stage of the preparation. For example, a gene encoding a selectable marker or other gene of interest can be introduced to the prepared stem cells.

To increase the growth of the stem cells, the stem cells are mixed with medium that has been incubated with placental tissue. By "incubation" any type of contact between said media and placental tissue or cells thereof is implied. The method described herein provides for a method of expansion of stem cells that in one embodiment does not require undefined culture medium. Further, the method described herein does not require a culture medium that contains animal products with unknown negative effects, such as, for example, increased antigenicity, or xoonosis.

Preparation and Incubation of the Placental Tissue

The placental tissue can be derived from fresh sources, or can have been stored prior to use. Storage can take place with the placenta as an intact unit, or a deaggrated unit, or as dissociated placental cells. One of skill in the art can determine the incubation medium to place the placental tissue in. Any suitable liquid can be used, such as for example a buffer, water such as isotonic water, or growth medium. Exemplary media include, but are not limited to, Iscove's modified Dulbecco's Media (IMDM) media, DMEM, KO-DMEM, DMEM/F12, RPMI 1640 medium, McCoy's 5A medium, minimum essential medium alpha medium (α-MEM), F-12K nutrient mixture medium (Kaighn's modification, F-12K), X-vivo 20, Stemline, CC100, H2000, Stemspan, MCDB 131 Medium, Basal Media Eagle (BME), Glasgow Minimum Essential Media, Modified Eagle Medium (MEM), Opti-MEM I Reduced Serum Media, Waymouth's MB 752/1 Media, Williams Media E, Medium NCTC-109, neuroplasma medium, BGJb Medium, Brinster's BMOC-3 Medium, CMRL Medium, CO2-Independent Medium, and Leibovitz's L-15 Media or other liquid as determined by one of skill in the art.

Any part of the placental tissue can be used for the incubation process. For example, the whole placenta can be incubated by submergence in the media which is desired to be conditioned, alternatively the incubation can occur by perfusion of the placenta with media which is desired to be conditioned. Perfusion can be performed through the fetal circulatory system via the umbilical vein and arteries, or through the maternal side in distinct placental cotyledons, or in a manner encompassing all of the maternal circulation. In a preferred embodiment the fetal circulation is perfused. Furthermore, distinct sections of the placenta can be used for the incubation. The sections can include but are not limited to isolated chorionic plate, chorionic villi, Wharton's Jelly, amniotic membranes, chorionic membranes or cotyledon units. Furthermore, distinct placentally derived cells can be isolated and used for incubation. Said cells include but are not limited to endothelial, epithelial, trophoblastic, macrophages, and mesenchymal cells. The placental tissue can be rinsed with an anticoagulation solution prior to incubation, if desired. Exemplary anticoagulation solutions include but are not limited to saline, a buffer, or media mixed with heparin, EDTA, antithrombin III, and the like.

The placental tissue to be used can be derived from any mammalian organism. Preferably, the placental tissue is derived from a human.

The placental incubation period can be determined by one of skill in the art. Generally, the placental incubation period can range from less than about 1 second, 30 seconds, or 60 seconds to about 2 or 3 weeks or more. Preferably, the placental incubation period is between about 2, 5, 10, 30, or 45 minutes to about 12, 14, 16, 18, or 20 days. More preferably, the placental incubation period is between about 1, 3, 5, 8, or 24 hours to about 3, 5, 7, or 10 days.

The preferred temperature for the placental incubation process can be from a range of about 32° C. or less to about 40° C. or more. Preferably, the placental incubation occurs at a temperature of about 33° C., 34° C., or 35° C. to about 38° C., 39° C., or 40° C. More preferably, the placental incubation occurs at about 37° C. The incubation medium can be changed regularly, if desired.

The placental incubation medium can be mixed, if desired, at any suitable speed. Any suitable container can be used.

Antibiotics, antifungals or other contamination preventive compounds can be added to the incubation medium, if desired. Exemplary compounds include but are not limited to penicillin, streptomycin, gentamycin, fungizone or others known in the art.

The live placenta conditioned medium (LPCM) so produced can then be filtered, if desired. Preferably, the filtration process occurs through a sterile 0.2 μm filter. Additionally, other types of filters can be used depending on the desired sterility of the LPCM. In some situations filters with nano-sized pores can be useful in order to prevent viral contamination. Additionally, methods known in the art for decontamination can be used such as UV irradiation, X-ray sterilization, ozonation, or hyperthermia in order to selectively destroy potential contaminants without losing the desired biological activity of the LPCM. An example of the placental incubation process is shown in Example 1.

The LPCM can be stored in a variety of manners prior to use, this includes lyophilized, frozen, stored under refrigerated conditions, stored in combination with a preservative agent, or by other means known to one skilled in the art. It is desired that the storage step does not effect properties that fresh LPCM would bestow during incubation with stem cells.

Contacting the Stem Cells with the LPCM

The prepared stem cells can be contacted with the LPCM. This can be done, for example, by simply mixing the LPCM with the culture of stem cell preparations. Mixing can be performed in a plethora of suitable vessels capable of maintaining viability of the stem cells. Said vessels can include but are not limited to tissue culture flasks, conical tubes, culture bags, bioreactors, or cultures that are continuously mixed. The stem cell/LPCM mixture can then be allowed to grow as desired. An example of stem cell growth in the stem cell/LPCM mixture is shown in Example 3. In some situations it will be desirable to use a combination culture system in which cells are first grown with one type of culture condition, then subsequently another culture condition is used. For example, when rapid expansion of hematopoietic stem cells is needed without differentiation, cells can be cultured initially in a high concentration of LPCM for 48 hours, or a time period needed to induce cycling of the stem cells. Subsequently, media containing cytokines can be added in the culture for passages after the first 48 hours. Cytokine media can be DMEM supplemented with a combination of IL-3, IL-6, SCF, TPO, and flt-3L. One skilled in the art will understand that depending on stem cell type and level of differentiation desired, different concentrations of LPCM can be added at the different time points of the culture. For example, in a particular culture situation, addition of LPCM at the initiation of culture can not be optimum. In the case that cardiomyocytes are desired from embryonic stem cells, addition of LPCM to the embryonic stem cell culture will only increase the number of undifferentiated stem cells and not allow cardiomyocyte differentiation, even if differentiation-promoting stimuli are added. Accordingly, the optimum use of LPCM in this situation is after differentiation, or partial differentiation along the cardiomyocyte lineage has occurred. In a practical example, human embryonic stem cells are cultured on mitotically inactivated (mitomycin C) murine embryonic feeder layers in culture medium consisting of 80% knockout DMEM (no-pyruvate, high-glucose formulation; Life Technologies Inc., Rockville, Md., USA) supplemented with 20% FBS (Hy-Clone, Logan, Utah, USA), 1 mM L-glutamine, 0.1 mM mercaptoethanol, and 1% nonessential amino acid stock (all from Life Technologies Inc) If LPCM is added (at concentrations ranging from about 2-10 Units/ml, Example 4) to this culture, there is an accelerated growth of embryonic stem cells but no differentiation.

In order to induce cardiomyocyte generation embryonic stem cells are generally dispersed to small clumps (three to 20 cells) using collagenase IV (Life Technologies Inc.; at a concentration of about 1 mg/ml for 20 minutes). Cells can then be transferred to plastic Petri dishes (Miniplast, Ein Shemer, Israel), at a cell density of about $5 \times 10^6$ cells in a 58-mm dish, where they are cultured in suspension (using same media as above) for 7-10 days. During this stage, the cells aggregated to form embryoid bodies, which are then plated on 0.1% gelatin-coated culture dishes, at a density of one to five embryoid in a 1.91-cm$^2$ well, and observed microscopically for the appearance of spontaneous contractions. If LPCM (2-10 Units/ml) is added at the period of day 1-5 of liquid culture, an increased cellularity is observed but a significant decrease in spontaneously beating embryoids is observed in the gelatin coated dishes. In contrast, if LPCM is added at days 6-7 of the liquid culture, then the number of contracting embryoids on gelatin is generally increased about 4-fold compared to cultures lacking LPCM. This illustrates that under some culture conditions LPCM is capable of inducing proliferation of cells at a specific level of differentiation, and that in some circumstances LPCM can actually inhibit differentiation even in the presence of conditions that would normally stimulate it.

The desired ratio of stem cells to LPCM can be determined by one of skill in the art. For example, a ratio of less than about 1:1,000, to 1,000:1 or more (stem cell preparation to LPCM) can be used. For example, a ratio of stem cell preparation to LPCM from about 1:750, 1:500, 1:250, or 1:100 to about 100:1, 250:1, 500:1, or 750:1 can be used. This ratio can vary, for example, depending on temperature, incubation time, number of stem cells, the desired activity sought in the stem cells, the type of stem cells, the purity of stem cells, the amount of placental tissue used as a starting point, and the like. The stem cells can be isolated from their growth media prior to contacting with the LPCM, or the stem cells can remain in their growth medium, with the LPCM added.

The length of the stem cell/LPCM contacting step can be determined by one of skill in the art. Generally, the contacting step can range from less than about 1 second, 30 seconds, or 60 seconds to about 2 or 3 weeks or more, Preferably, the contacting step is between about 2, 5, 10, 30, or 45 minutes to about 12, 14, 16, 18, or 20 days. More preferably, the contacting step is between about 1, 3, 5, 8, or 24 hours to about 3, 5, 7, or 10 days.

In some embodiments, other compounds can be added to the stem cell/LPCM mixture. For example, growth factors can be added to the mixture. Exemplary factors include but are not limited to thrombopoietin (TPO), stem cell factor (SCF), IL-1, IL-3, IL-7, flt-3 ligand (flt-3L), G-CSF, GM-CSF, Epo, FGF-1, FGF-2, FGF-4, FGF-20, IGF, EGF, NGF, LIF, PDGF, bone morphogenic proteins (BMP), activin-A, VEGF, forskolin, glucocorticoids, and the like. Specific concentrations and activities are known to one skilled in the art. For reference as to applicability to stem cell, the practitioner of the invention is referred to the following publications: TPO (Kawada, et al., 1999, *Exp Hematol* 27:904-915; Wang, et al., 2005, *Ann NY Acad Sci* 1044:29-40; Xie, et al., 2003, *Blood* 101:1329-1335; Feugier, et al., 2002, *J Hematother Stem Cell Res* 11:127-138; Won, et al., 2000, *J Hematother Stem Cell Res* 9:465-473), SCF (Wang, et al., 2005, *Cell Biol Int* 29:654-661; Levac, et al., 2005, *Haematologica* 90:166-172; Peschle, et al., 1993, *Stem Cells* 11:356-370), IL-1 (Maurer, et al., 2000, *Int J Hematol* 71:203-210; Willems, et al., 2001. *Ann Hematol* 80:17-25; Scheding, et al., 2000, *Exp Hematol* 28:460-470), IL-3 (Ivanovic, Z., 2004, *Eur Cytokine Netw* 15:6-13; Inderbitzin, et al., 2005, *J Gastrointest Surg* 9:69-74; Bohmer, R. M., 2004, *Stem Cells* 22:216-224), IL-6 (Quesenberry, et al., 1991, *J Cell Biochem* 45:273-278; Zhang, et al. Increased myelinating capacity of embryonic stem cell derived oligodendrocyte precursors after treatment by interleukin-6/soluble interleukin-6 receptor fusion protein. *Mol Cell Neurosci.*, e-published on Nov. 30, 2005; Taga, et al., 2005, *Clin Rev Allergy Immunol* 28:249-256; Nakamura, et al., 2005, *Clin Rev Allergy Immunol* 28:197-204), IL-7 (Ficara, et al., 2004, *Mol Ther* 10:1096-1108; Krawczenko, et al., 2005, *Arch Immunol Ther Exp (Warsz)* 53:518-525; Andre-Schmutz, et al., 2004, *Br J Haematol* 126:844-851; De Waele, et al., 2004, *Eur J Haematol* 72:193-202), IL-11 (Willems, supra; Lu, et al., 2003, *Zhonghua Xue Ye Xue Za Zhi* 24:589-592; Momose, et al., 2002, *Arzneimittelforschung* 52:857-861; Van der Meeren, et al., 2002, *Radiat Res* 157:642-649), flt-3L (Li, et al., 2005, *Eur J Haematol* 74:128-135; McGuckin, et al., 2004, *Cell Prolif* 37:295-306; Lu, et al., *Blood* 103:4134-4141; Streeter, et al., 2003, *Exp Hematol* 31:1119-1125), G-CSF (Aliotta, et al., 2006, *Exp Hematol* 34:230-241; Jung, et al. Granulocyte colony-stimulating factor stimulates neurogenesis via vascular endothelial growth factor with STAT activation. *Brain Res.*, e-published on Jan. 16, 2006; Kogler, et al., 2005, *Exp Hematol* 33:573-583), GM-CSF (Quesenberry, supra; Gangenahalli, et al., 2005, *Stem Cells Dev* 14:140-152), Epo (Otani, et al., 2004, *Exp Hematol* 32:607-613; Yao, et al., 2000, *Bone Marrow Transplant* 26:497-503; Mobest, et al., 1998, *Biotechnol Bioeng* 60:341-347), FGF-1 (de Haan, supra; Crcareva, et al., 2005, *Exp Hematol* 33:1459-1469), FGF-2 (Ratajczak, et al., 1996, *Br J Haematol* 93:772-782; Kang, et al., 2005, *Stem Cells Dev* 14:395-401), FGF-4 (Schwartz, et al., 2005, *Stem Cells Dev* 14:643-655; Quito, et al., 1996, *Blood* 87:1282-1291), FGF-20 (Grothe, et al., 2004, *Neurobiol Dis* 17:163-170), IGF (McDevitt, et al., 2005, *J Mol Cell Cardiol* 39:865-873; Musaro, A., 2005, *Arch Ital Biol* 143:243-248; Zumkeller, et al., 1999, *Blood* 94:3653-3657; Okajima, et al., 1998, *J Biol Chem* 273:22877-22883), EGF (Miyazaki, et al., 2004, *Cell Transplant* 13:385-391; von Ruden, et al., 1988, *Embo J* 7:2749-2756), NGF (Bracci-Laudiero, et al., 2003, *J Neuroimmunol* 136:130-139; Simone, et al., 1999, *Hematol Oncol* 17:1-10), LIF (Guo, et al. Murine Embryonic Stem Cells Secrete Cytokines/Growth Modulators that Enhance Cell Survival/Anti-Apoptosis and Stimulate Colony Formation of Murine Hematopoietic Progenitor Cells. *Stem Cells*, e-published on Dec. 8, 2005; Chodorowska, et al., 2004, *Ann Univ Mariae Curie Sklodowska [Med]* 59:189-193), PDGF (Su, et al., 2005, *Stem Cells Dev* 14:223-230; Lucarelli, et al., 2003, *Biomaterials* 24:3095-3100; Yang, et al., 1995, *Br J Haematol* 91:285-289), BMPs (Ploemacher, et al., 1999, *Leukemia* 13:428-437; Zhang, et al., 2005, *Dev Biol* 284:1-11; Jay, et al., 2004, *Cell Res* 14:268-282; Chadwick, et al., 2003, *Blood* 102:906-915; Dormady, et al., 2001, *J Hematother Stem Cell Res* 10:125-140), activin-A (Shav-Tal, et al., 2002, *Stem Cells* 20:493-500), VEGF (Cerdan, et al., 2004, *Blood* 103:2504-2512), forskolin (Laharrague, et al., 1998, *Faseb J* 12:747-752; Gaspar Elsas, et al., 2000, *Br J Pharmacol* 130: 1362-1368), and glucocorticoids (Grafte-Faure, et al., 1999, *Am J Hematol* 62:65-73), each of which is incorporated by reference herein in its entirety.

Furthermore, conditions promoting certain type of cellular proliferation or differentiation can be used during the culture. These conditions include but are not limited to, alteration in temperature, alternation in oxygen/carbon dioxide content, alternations in turbidity of said media, or exposure to small molecules modifiers of cell cultures such as nutrients, inhibitors of certain enzymes, stimulators of certain enzymes, inhibitors of histone deacetylase activity such as valproic acid (Bug, et al., 2005, *Cancer Res* 65:2537-2541), trichostatin-A (Young, et al., 2004, *Cytotherapy* 6:328-336), trapoxin A (Kijima, et al., 1993, *J Biol Chem* 268:22429-22435), or Depsipeptide (Gagnon, et al., 2003, *Anticancer Drugs* 14:193-202; Fujieda, et al., 2005, *Int J Oncol* 27:743-748), each of which is incorporated by reference herein in its entirety, inhibitors of DNA methyltransferase activity such as 5-azacytidine, inhibitors of the enzyme GSK-3 (Trowbridge, et al., 2006, *Nat Med* 12:89-98, which is incorporated by reference herein in its entirety), and the like.

A variety of factors previously mentioned influence ability of stem cells to survive, replicate, and differentiate. For example, in terms of nutrients the amino acid taurine under certain conditions preferentially inhibits murine bone marrow cells from forming osteoclasts (Koide, et al., 1999, *Arch Oral Biol* 44:711-719), the amino acid L-arginine stimulates erythrocyte differentiation and proliferation of erythroid progenitors (Shima, et al., 2006, *Blood* 107:1352-1356), extracellular ATP acting through P2Y receptors mediates a wide variety of changes to both hematopoietic and non-hematopoietic stem cells (Lee, et al., 2003, *Genes Dev* 17:1592-1604), arginine-glycine-aspartic acid attached to porous polymer scaffolds increase differentiation and survival of osteoblast progenitors (Hu, et al., 2003, *J Biomed Mater Res A* 64:583-590), each of which is incorporated by reference herein in its entirety. Accordingly, one skilled in the art would know to use various types of nutrients for inducing differentiation, or maintaining viability, of certain types of stem cells and/or progeny thereof.

The role of oxygen tension in stem cell self-renewal and viability is also an important issue that is contemplated in the current invention. It is known that hematopoietic stem cells tend to reside in hypoxia niches of the bone marrow and that as cells differentiate into more mature progeny, they progressively migrate to areas of the bone marrow with higher oxygen tension (Ivanovic, et al., 2002, *Exp Hematol* 30:67-73, which is incorporated by reference herein in its entirety). This important variable in tissue culture was exploited in studies showing that superior expansion of human CD34 stem cells capable of full hematopoietic reconstitution of NOD-SCID mice were obtained in hypoxic conditions using oxygen tension as low as 1.5%. The potent expansion under hypoxia, which was 5.8-fold higher as compared to normal oxygen tension, was attributed to hypoxia induction of HIF-1 dependent growth factors such as VEGF (Danet, et al., 2003, *J Clin Invest* 112:126-135, which is incorporated by reference herein in its entirety). Additionally, other stem cells such as neuronal stem cells also appear to be localized in hypoxic niches and expand preferential in low oxygen in vitro conditions as opposed to normal oxygen tension (Zhu, et al., 2005, *Mol Neurobiol* 31:231-242, which is incorporated by reference herein in its entirety). Furthermore, embryonic stem cells, although grow at similar proliferative rates between normoxia and hypoxia, they retain superior ability to form teratomas in vivo and embryoid bodies in vitro when grown under hypoxic conditions (Ezashi, et al., 2005, *Proc Natl Acad Sci USA* 102:4783-4788, which is incorporated by reference herein in its entirety).

Accordingly, one embodiment of the disclosed invention is the use of hypoxic conditions for augmenting release of stem cell proliferating factors in the placenta during production of LPCM. Hypoxic conditions can be maintained in specialized incubators with an oxygen tension ranging from 0.1% to 7.5%, preferably 0.5% to 5%, more preferably 3%-5%. Additionally, another embodiment of the invention is the use of hypoxic conditions in combination with LPCM in order to enhance proliferation without differentiation of stem cells being grown in culture.

In terms of enhancing the ability of LPCM to stimulate proliferation of stem cells without differentiation, one adjuvant approach that is considered an embodiment of the invention is the use of enzymatic inhibitors in conjunction with LPCM. For example, histone deacetylases are a class of enzymes involved in epigenetically opening parts of chromatin to transcription factors, thus allowing expression of genes that under normal adult conditions would not be expressed. For example, the telomerase gene (catalytic subunit hTERT) is involved in the process of cellular immortalization and is expressed under physiological conditions only in embryonic stem cells, as well as some bone marrow hematopoietic cells, abnormally. The functional role of the telomerase enzyme is to repair the shortened telomeric ends of chromosomes so that cells can escape replicative senescence. Pathologically, telomerase is the enzyme responsible for the ability of cancer cells to proliferate indefinitely in cell culture, Under normal physiological conditions fibroblasts do not express telomerase and undergo replicative senescence. A variety of reports have been published describing that treatment of fibroblasts with histone deacetylase inhibitors such as trichostatin A reinduces expression of functional telomerase (Mukhopadhyay, et al., 2005, *J Cell Mol Med* 9:662-669; Hou, et al., 2002, *Exp Cell Res* 274:25-34; Cong, et al., 2000, *J Biol Chem* 275:35665-35668, each of which is incorporated by reference herein in its entirety). This is suggestive that manipulating the histone deacetylase pathway can be used as a method of de-differentiating cells or offering the possibility of "rejuvenating" progenitors that are nearing replicative exhaustion. Indeed, it was demonstrated that the life extension effect observed due to caloric restriction is connected to the histone deacetylase pathway (Howitz, et al., 2003, *Nature* 425:191-196, which is incorporated by reference herein in its entirety). The clinical relevance of manipulating this pathway is illustrated in experiments with valproic acid, an antidepressant that is in clinical use is a histone deacetylase inhibitor with similar potency to trichostatin A in some models. It was demonstrated that treatment of bone marrow derived hematopoietic stem cells with valproic acid increases both proliferation and self-renewal through accelerating cell cycle progression (Bug, supra). Said acceleration was accompanied by a down-regulation of inhibitor factor p21(cip-1/waf-1). Furthermore, valproic acid treatment suppressed GSK3 activity and activated the Wnt signaling pathway, both of which are associated with self renewal in both hematopoietic (Gotoh, et al., 1997, *Cell Growth Differ* 8:721-729; Baba, et al., 2005, *Immunity* 23:599-609, each of which is incorporated by reference herein in its entirety), but also embryonic (Sato, et al., 2004, *Nat Med* 10:55-63; He, et al., 2005, *Clin Lung Cancer* 7:54-60, each of which is incorporated by reference herein in its entirety) stem cells. The potency of valproic acid to synergize with known hematopoietic stem cell stimulatory cytokines such as Flt3L, TPO, SCF and IL-3 was demonstrated (De Felice, et al., 2005, *Cancer Res* 65:1505-1513, which is incorporated by reference herein in its entirety).

Based on the above discussion, it is apparent to one skilled in the art that combinations of histone deacetylase inhibitors in conjunction with LPCM can be useful for expansion of stem cells not only in vitro, but also in vivo. For example, in an embodiment of the current invention, the histone deacetylase inhibitor valproic acid is administered at a concentration ranging from 20 mg/day to 1,500 mg/day on a daily basis in conjunction with 20-500 Units of LPCM per day in a patient in whom hematopoietic reconstitution is sought. More preferably, a dose of 150 mg/day to 1,000 mg/day is given in conjunction with a dose of 100-300 Units of LPCM/day, even more preferably, a dose of 750 mg/day of valproic acid is given in conjunction with 250 Units of LPCM. One skilled in the art will understand to vary the dose based on certain characteristics of the patient, such as tolerability to valproic acid, as well as amount and rapidity of hematopoietic reconstitution that is required. Similar treatments can be used for enhancing the proliferation and expansion of endogenous stem cells in diseased situations. For example, patients suffering from a stem cell insufficiency in smooth muscle tissue, striated muscle tissue, cardiac muscle tissue, bone tissue, bone spongy tissue, cartilage tissue, pancreatic ductal tissue, spleen tissue, thymus tissue, tonsil tissue, Peyer's patch tissue, lymph nodes tissue, thyroid tissue, epidermis tissue, dermis tissue, subcutaneous tissue, heart tissue, lung tissue, vascular tissue, endothelial tissue, blood cells, bladder tissue, kidney tissue, digestive tract tissue, esophagus tissue, stomach tissue, small intestine tissue, large intestine tissue, adipose tissue, uterus tissue, eye tissue, lung tissue, testicular tissue, ovarian tissue, prostate tissue, connective tissue, endocrine tissue, and mesentery tissue can be treated with an agent that mobilizes endogenous stem cells, such as G-CSF, GM-CSF, or antagonist of CXCR-4, in combination with a histone deacetylase inhibitor and LPCM. Additionally, local concentrations of LPCM can be added in combination with a histone deacetylase inhibitor in the tissue in need thereof. Localization can be achieved through the use of certain delivery polymers known to one who is skilled in the art. These can include, but are not limited to, polyvinyl chloride, polylactic acid (PLA), poly-L-lactic acid (PLLA), poly-D-lactic acid (PDLA), polyglycolide, polyglycolic acid (PGA), polylactide-co-glycolide (PLGA), polydioxanone, polygluconate, polylactic acid-polyethylene oxide copolymers, polyethylene oxide, modified cellulose, collagen, polyhydroxybutyrate, polyhydroxpriopionic acid, polyphosphoester, poly(alpha-hydroxy acid), polycaprolactone, polycarbonates, polyamides, polyanhydrides, polyamino acids, polyorthoesters, polyacetals, polycyanoacrylates, degradable urethanes, aliphatic polyester polyacrylates, polymethacrylate, acyl substituted cellulose acetates, non-degradable polyurethanes, polystyrenes, polyvinyl flouride, polyvinyl imidazole, chlorosulphonated polyolifins, polyvinyl alcohol, and the like. Other suitable polymers can be obtained by reference to The Polymer Handbook, 3rd edition (Wiley, N.Y., 1989). In addition, specific growth factors can also be added, guided by the type of stem cell desired and amount of proliferation/differentiation. Said growth factors can include can include members of the insulin like growth factor family, the wingless related factor family, the nerve growth factor family and the hedgehog factor family. Other specific growth factors can include brain derived neurotrophic factor, neurotrophin-3, neurotrophin-4/5, ciliary neurotrophic factor, cardiotrophin, members of the transforming growth factor (TGF)/bone morphogenetic protein/growth and differentiation factor family, the glial derived neurotrophic factor family including but not limited to neurturin, neublastin/artemin, and persephin and factors related to and including hepatocyte growth factor.

In a preferred embodiment, LPCM is generated using IMDM as a perfusion solution, however the IMDM is supplemented with a serum substitute such as commercially available mixtures including, but not limited to BIT9500 (Stem Cell Technologies, Vancouver Canada). In other embodiments, the serum substitute is comprised of bovine serum albumin (BSA), insulin, and transferrin (TF). Alternatively, human serum albumin USP can be used in cultures intended for clinical use. The serum substitute can be comprised of, for example, about 0.1 to about 0.50 g/liter of human serum albumin, about 0.01 to about 1,000 µg/ml insulin, and about 0.1 to about 1,000 µg/ml transferrin. In another more preferred embodiment the serum substitute can be comprised of 4 g/liter of human serum albumin, about 0.71 µg/ml of insulin and about 27 µg/ml of transferrin. One of skill in the art will understand that depending on the cells which are intended for culture, or the desired properties of the LPCM, various concentrations can be experimentally assessed and tailored according to the biological response sought.

In addition, a variety of cytokines can be added to the perfusing solution during production of LPCM. In one embodiment the following cytokines are used: TPO, SCF, Flt-3L, IL-3, IL-6, IL-11, G-CSF and GM-CSF. In a preferred embodiment, a concentration of about 0.1-500 ng/ml TPO, about 0.1-500 ng/ml SCF, about 0.1-500 ng/ml Flt3L, about 0.1-700 ng/ml IL-3, about 0.1-700 ng/ml IL-6, about 0.1-500 ng/ml IL-11, about 0.1-500 ng/ml G-CSF, and about 0.1-500 ng/ml GM-CSF is used. In a more preferred embodiment, DMEM is used as a starting solution for perfusion and is supplemented with the cytokine cocktail of: about 20 ng/ml IL-3, about 250 ng/ml IL-6, about 10 ng/ml SCF, about 250 ng/ml TPO, and about 100 ng/ml flt-3L.

By treatment with LPCM, the stem cells are able to increase their growth rate and expand rapidly. When desired, culture conditions are used that preferentially allow the LPCM to augment proliferation of stem cells without induction of differentiation. Any suitable method of determining the growth rate and differentiation of the stem cells can be used to determine the growth rate and cell count of the stem cells so produced. For example, flow cytometry analysis of markers associated with stem cell retention, LTC-IC and semisolid media assays for quantification of early and committed progenitors, and in vivo NOD-SCID Repopulating Activity Assays to quantify the number of in vivo stem cells with reconstituting activity. Said assays can be modified and altered in order to allow detection of specific stem cell subtypes. Assays can also be developed in immune compromised mice, such as the NOD-SCID strain, by induction of a pathology to which the human stem cells is anticipated to be therapeutics. For example, human stem cells have been demonstrated to possess therapeutic activity in a variety of non-hematopoietic settings in the NOD-SCID, as well as the NUDE mouse. Other models of immunodeficiency are known to one skilled in the art and include the NK deficient beige mouse, the T cell and B cell deficient RAG knockout mouse, and the common gamma chain knockout mouse. Furthermore, such immunodeficient mouse strains can be selectively bred with strains possessing a certain disease pathology so as to assess the effect of human stem cells expanded by LPCM in them.

As shown in Example 3, the use of the LPCM method is capable of greatly increasing the stem cell growth rate. The cell growth rate can also depend on other factors, such as, for example, temperature, type of stem cell, contents of the medium, and the time allowed for the placental incubation step and contacting step. One of skill in the art will be able to alter these variables to adjust the growth rate as needed.

Another embodiment of the invention is a pharmaceutical preparation comprising LPCM generated in a Good Manufacturing Practices/Good Tissue Practices environment that will allow it to be suitable for clinical use. LPCM is generated by perfusing placentas in an environment that is sterile, using a perfusate media that does not contain animal proteins or underdefined components. Such a media can be X-VIVO 10 or other clinically applicable medias. Subsequent to concentration and quantification of units of activity, said LPCM can be diluted into an excipient or carrier. For practical use, will be advantageous to formulate compositions in dosage unit form for ease of administration and uniformity of dosage. Dosage unit form as used herein refers to physically discrete units suited as unitary dosages for an individual to be treated; each unit containing a predetermined quantity of active compound calculated to produce the desired therapeutic effect in association with the required pharmaceutical carrier. The dosage unit forms of the invention are dependent upon the amount of a compound necessary to stimulate proliferation of the respective stem cells whose proliferation and/or differentiation is being sought. The amount of a compound necessary to stimulate proliferation and/or differentiation of the desired stem cells can be formulated in a single dose, or can be formulated in multiple dosage units. Treatment can require a one-time dose, or can require repeated doses.

Actual formulation of the LPCM will be performed in agreement with standard practices that are known to one skilled in the art. These are well known in the art and the one chosen is based upon the route of administration that will be used, as well as specific pharmacokinetic properties that are desired. For example, the preferred embodiment of an LPCM-based therapy is an injectable, more preferred an injection into the specific area requiring regeneration of stem cells. However, several embodiments are possible. For example, routes of administration can include parenteral, e.g., intravenous, intradermal, subcutaneous, oral (e.g., ingestion or inhalation), transdermal (topical), transmucosal, and rectal administration. Solutions or suspensions for formulating an LPCM-based therapeutic can include: sterile diluent such as water for injection, saline solution (e.g., phosphate buffered saline (PBS, UPS)), fixed oils, glycerine, or other synthetic solvents; antibacterial and antifungal agents such as parabens, a polyol (for example, glycerol, propylene glycol, and liquid polytheylene glycol, and the like), chlorobutanol, phenol, ascorbic acid, thimerosal, and the like; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The desired fluidity can be maintained, for example, by the use of a coating such as lecithin, by the maintenance of the required particle size in the case of dispersion and by the use of surfactants. In many cases, it will be preferable to include isotonic agents, for example, sugars, sodium chloride, polyalcohols such as mannitol or sorbitol, and in the composition. Prolonged administration of the injectable compositions can be brought about by including an agent that delays absorption. Such agents include, for example, aluminum monostearate and gelatin. The parenteral preparation can be enclosed in ampules, disposable syringes, or multiple dose vials made of glass or plastic. It is known in the art, and common practice for oral compositions to generally include an inert diluent or an edible carrier. Oral compositions can be liquid, or can be enclosed in gelatin capsules or compressed into tablets. Tablets, pills, capsules, troches and the like can contain any of the following ingredients, or compounds of a similar nature: a binder such as microcrystalline cellulose, gum tragacanth or gelatin; an excipient such as starch or lactose; a disintegrating agent such as alginic acid, Primogel, or corn starch; a lubricant such as magnesium stearate or Sterotes; colloidal silicon dioxide. Transmucosal administration can be accomplished through the use of nasal sprays or suppositories. For transdermal administration, the active compounds are formulated into ointments, salves, gels, or creams as generally known in the art.

EXAMPLES

The following examples are offered to illustrate, but not to limit, the claimed invention.

Example 1

Incubation of Placenta in Growth Medium

A fresh human placenta obtained from vaginal delivery was placed in a sterile plastic container. The placenta was rinsed with an anticoagulant solution comprising phosphate buffered saline (Gibco-Invitrogen, Grand Island, N.Y.), containing a 1:1000 concentration of heparin (1% w/w) (American Pharmaceutical Partners, Schaumburg, Ill.).

The placenta was then covered with a DMEM media (Gibco) in a sterile container such that the entirety of the placenta was submerged in said media, and incubated at 37° C. in a humidified 5% $CO_2$ incubator for 24 hours. At the end of the 24 hours, the live placenta conditioned medium (LPCM) was isolated from the container and sterile-filtered using a commercially available sterile 0.2 micron filter (VWR).

Example 2

Isolation of CD 34+ Cells from Human Umbilical Cord Blood and Subsequent Growth of Cells Approximately 40 ml of cord blood was collected from a human umbilical cord via venipuncture and allowed to drop by gravitational force into a 250 ml sterile bag containing 20 ml citrate-phosphate-dextrose under sterile conditions. Collected blood cells were layered onto 50 ml conical tubes containing Ficoll-Hypaque (density 1.077 gram/ml; Sigma, St Louis, Mo.) and centrifuged at 400×g for 30 minutes. The mononuclear cells in the interface layer were then collected, washed three times in PBS, and re-suspended in PBS solution containing 0.5% serum albumin. CD34+ cells were purified from the mononuclear cell fraction by immuno-magnetic separation using the Magnetic Activated Cell Sorting (MACS) CD34+ Progenitor Cell Isolation Kit (Miltenyi-Biotec, Auburn, Calif.) according to manufacturer's recommendations. The purity of the CD34+ cells obtained ranged between 95% and 98%, based on Flow Cytometry evaluation (FACScan flow cytometer, Becton-Dickinson, Immunofluorometry systems, Mountain View, Calif.). Cells were plated at a concentration of $10^4$ cells/ml in a final volume of 0.5 ml in 24 well culture plates (Falcon; Becton Dickinson Biosciences) in DMEM. Four different treatment groups were used. Group 1 consisted of cells in DMEM with no growth factor supplementation. Group 2 consisted of cells in DMEM supplemented with the cytokine cocktail of: 20 ng/ml IL-3, 250 ng/ml IL-6, 10 ng/ml SCF, 250 ng/ml TPO and 100 ng/ml flt-3L. Group 3 consisted of cells in the cytokine cocktail, with a 50% mixture of LPCM. LPCM was generated as described in Example 1. Group 4 consisted of cells spun down and resuspended in 100% LPCM. Cells were cultured for 10 days at 37° C. in a fully humidified 5% $CO_2$ incubator. The respective media was added to each group once every three days at a volume of 0.5 ml. Subsequent to incubation, cells were collected and numbers of viable CD34+ cells were assessed by flow cytometry using FITC-conjugated anti-human CD34 antibodies (Beckman Coulter) and the viability dye propidium iodine (Invitrogen). Cells in Group 1 had a decreased number of viable CD34+ cells. Of the approximate $5 \times 10^3$ cells inoculated in the starting culture, output at 10 days was $5\text{-}10 \times 10^2$ viable CD34+ cells. In contrast, Group 2 had an approximate 50-80 fold increase in the number of viable CD34+ cells collected at the end of culture as compared with the original input of $5 \times 10^3$ cells. Viable CD34+ cells in Group 3 were synergistically expanded by the combination of growth factors and LPCM in that the output cell numbers were 300-500 times higher than the input. The ability of LPCM to induce proliferation of CD34+ cells in absence of growth factor addition was demonstrated in that the cells of Group 4 were expanded 50-100 fold at the end of culture. These data demonstrate that LPCM can act as a source of growth factors on its own, but can also synergize potently with existing growth factor combinations. Importantly, the fact that no addition of human proteins was needed for this potent expansion of CD34+ stem cells is indicative of the utility of LPCM for a variety of stem cell applications.

Example 3

Expansion of Stem Cells

At the end of the 24 hour period, the LPCM from Example 1 was added to the wells of the sterile 24 well tissue culture plate in a volume of 0.25 ml. Umbilical cord mononuclear cells harvested as described in Example 1 were resuspended in DMEM in a volume of 0.25 ml and added to the wells containing LPCM. The final concentration of mononuclear cells was $10 \times 10^6$ cells per ml. The cultures were subsequently incubated for an additional seven days at 37° C. in a humidified 5% $CO_2$ incubator. The number of CD 34+ cells and viability was then determined by flow cytometry as described in Example 2 both at the beginning of cell culture and subsequently after 7 days of culture. The number of viable CD34+ cells had increased 27.4 fold over the starting number of cells. In contrast, cells that were cultured with DMEM media alone in absence of LPCM had a decline in viable CD34+ cell numbers by approximately 7 fold.

Example 4

Generation, Quantification, and Concentration of LPCM

A fresh human placenta obtained from vaginal delivery was placed in a sterile plastic container. The placenta was rinsed with an anticoagulant solution comprising phosphate buffered saline (Gibco-Invitrogen, Grand Island, N.Y.), containing a 1:1000 concentration of heparin (1% w/w) (American Pharmaceutical Partners, Schaumburg, Ill.). The umbilical arteries and the umbilical vein were identified and isolated. Initially, a solution of heparinized PBS was used to identify patent blood vessels capable of use for perfusion. The perfusion of vessels was accomplished by injection of 20 ml of heparinized PBS at a flow rate of approximately 20 ml per minute into the umbilical arteries. It was relatively easy to discriminate between the artery and veins based on the blood filled appearance of the veins. Once patency and suitability of blood vessels was identified, the vessels were cannulated using a sterile cannula connected to the tubing of a pulsitile pumping apparatus. The pump was connected to a collection flask and arranged as a continous circuit with a total volume of 50 ml of DMEM being perfused through the placenta. The cannulated placental unit was incubated in a fully humidified environment for 24 hours at 5% $CO_2$ at 37° C. The perfusion rate was 10 ml per minute at a pressure of 60 Hg.

Subsequent to incubation, medium was collected used as a source of LPCM. LPCM was sterilized using 0.2 micron filters (VWR) and frozen for future use. In order to quantitate biological activity, dilutions of LPCM in the following ratios by volume 1:1, 1:10, 1:100, 1:1000, were made in DMEM in absence of fetal calf serum or other serum sources, and the diluted media was added to a 200 µL culture of $5 \times 10^3$ human cord blood isolated CD34+ cells per well in 96 well plates in a 48 hour culture condition. The proliferation of these cells was quantitated by the tritiated thymidine method. Briefly, 1 µCi of [$^3$H]thymidine (Amersham) was added to each well for the last 12 h of culture. At the end of the culture period, using an automated cell harvester, the cells were collected onto glass microfiber filter, and the radioactive labeling incorporation was measured by a Wallac Betaplate liquid scintillation counter. 1 Unit of LPCM activity was designated as the amount of LPCM needed to stimulate proliferation of cord blood derived CD34+ cells by 100% higher than said cells in DMEM alone. Calculations are made on a logarithmic curve as described for other biological agents whose activity is quantitated in Units (DeKoter, et al., 1997, *Cell Immunol* 175:120-127, which is incorporated by reference herein in its entirety).

In order to concentrate LPCM, a volume of 40 ml of media was lyophilized under sterile conditions. Lyophilate was subsequently dialyzed using an exclusion of 5000 Daltons in order to extract salts and other small molecules in the solution. Reconstitution was performed in various volumes of USP saline and sterility as well as activity was quantified. Based on activity as measured using the CD34+ stimulation assay, various batches of LPCM were manufactured which are used for some of the experiments described below. Manufacturing of LPCM in this manner provided a non-toxic substance in that no maximally tolerated dose was observed when injecting C3H mice at concentrations ranging up to $1 \times 10^6$ Units. Toxicity was evaluated at the histological level after acute and chronic administration, as well as by enzymatic markers of organ damage such as creatinine, myocardial kinase, troponin, transaminases, and albumin secretion. Furthermore, no pyrogenicity was observed in any of the treated animals. Higher concentrations were not evaluated since one tenth of this dose is still substantially above what would be used in a clinical setting.

Example 5

Expansion of Embryonic Stem Cells in Feeder Free Cultures Using LPCM

The H1 human embryonic stem cell line is obtained from the Wi-Cell Research Institute (Madison, Wis.) and is propagated and cultured in mouse embryonic fibroblast (MEF)-conditioned medium (MEF-CM) containing 4 ng/ml human basic fibroblast growth factor (bFGF) (Life Technologies, Rockville, Md.) in six-well (35-mm-diameter) plates pre-coated with Matrigel (Becton-Dickenson Labware, Bedford, Mass.) and cultured at 37° C., under 5% $CO_2$ in Dulbecco's modified Eagle medium (DMEM)/F12 medium with 20% knockout serum replacement (KOSR), 1 mM L-glutamine, 1% nonessential amino acids, 0.1 mM 2-mercaptoethanol (2-ME), and 4 ng/ml bFGF (Invitrogen). Cells are harvested from tissue culture plates by digestion with 200 U/mL collagenase IV for 5 minutes at 37° C. and picking up individual colonies with a 20 microliter pipette tip under a microscope.

6-well plates tissue culture plates (Falcon) are coated with Matrigel™ (Becton Dickenson) and 10 colonies per well are added with 1 ml of either control DMEM media or LPCM. Cells are cultured for a period of 14 days after initial seeding, subsequently to which they are deaggregated using collagenase and stained for flow cytometric analysis of the embryonic stem cell markers SSEA-4. A two-fold increase in cells expressing SSEA-4 is observed in cultures treated with LPCM in comparison to DMEM treated cultures. When cells are maintained under similar conditions for extended cultures, such as for 120 days, the H-1 cells still possess ability to form multi-lineage teratomas upon injection of into NUDE mice. A higher expansion rate of H-1 cells is observed when cells are grown in LCMP media compared to DMEM on Matrigel™ cultures.

Example 6

Expansion of Amnionic Fluid-Derived Multipotent Stem Cells in Feeder Free Cultures Using LPCM Following a modification of the methodology described in U.S. Patent Application No. 2005/0054093, which is incorporated by reference herein in its entirety, approximately 5 ml of fresh amniotic fluid is collected during amniocentesis in the second trimester of pregnancy, mononuclear cells are pelleted by centrifugation and resuspended in either LPCM or DMEM. Cells are plated in 24 well plates at a concentration of $5 \times 10^3$ cells per well. Media is added every two days to the culture. After a period of 14 days an substantially increased number of cells positive for SSEA-3, and SSEA-4 as determined by flow cytometry are found in the cultures with LPCM, in contrast, cultures in DMEM appear to be populated by cellular debris and fibroblast like cells lacking stem cell markers (negative for SSEA-1, 3, 4, and CD34).

Example 7

Expansion of Cord Blood Derived Hematopoietic Cells in Liquid Culture

Cord blood CD34 cells are collected as described in Example 2. CD34+ cells are placed into 24-well plates (Falcon) at a concentration of 2000 cells per well. Each well contained 0.5 ml IMDM (Gibco) supplemented with BIT9500 (StemCell Technologies, Vancouver, Canada), instead of serum. Cytokines known to stimulate hematopoietic cell proliferation are added at the following concentrations: TPO (50 ng/ml), IL-3 (50 ng/ml), kit-ligand (100 ng/ml) and flt-3L (100 ng/ml). In some cultures 0.2 ml of IMDM is added, whereas in others LPCM generated using IMDM as a substitute for DMEM is added. The cultures are incubated at 37° C. in a humidified atmosphere containing 5% $CO_2$. On days 7 and 13, cells are harvested from the culture and are assayed for the number of erythroid burst-forming units (BFU-E), granulocyte-macrophage colony-forming units (CFU-GM) and mixed colony-forming units (CFU-Mix) are assayed using the methylcellulose semisolid culture system by the MethoCult7 kit according to the manufacturer's instructions (StemCell Technologies). Briefly, $1 \times 10^4$ CD34+ cells expanded in liquid culture (day 7 or 13) are plated into 35-mm plastic Petri-dishes (Falcon) in culture medium containing SCF, IL-3, G-CSF, GM-CSF and Epo as colony-stimulating factors in the presence of the semi-solid MethoCult methylcellulose base. As a comparison, freshly isolated CD34+ cells are added as an unstimulated control. Each dish is incubated at 37° C. in a humidified atmosphere of 5% $CO_2$ for 14 d. Colonies consisting of more than 50 cells are counted under an inverted microscope (Zeiss) and quantified. The total number of each type of progenitor cell is calculated from the total number of cells harvested and the number of each type of colony per well.

In comparison to day 0 CD34 cells, cells that are grown in liquid culture for 7 days generate a 150-fold expansion of CFU-GM when control IMDM media is added. In contrast, day 7 cultures supplemented with LPCM have a 440-fold expansion of CFU-GM. At 13 days of liquid culture there is a 550-fold expansion of CFU-GM in the IMDM media, whereas the LPCM supplemented cultures have a 790-fold expansion of CFU-GM. In terms of BFU-E there is a 300-fold expansion at day 7 of culture in IMDM control in contrast to the 700-fold expansion in the LPCM treated group. Similarly, at day 13, the control IMDM culture generated a 150-fold expansion of BFU-E in contrast to the LPCM treated group which had a 550-fold expansion. When assessing the earlier progenitor colonies, CFU-Mix, a 200-fold expansion is observed on day 7 in control treated cultures, whereas a 400-fold increase is observed in the LPCM-treated cultures. More strikingly is the effect at day 13 of liquid culture where CFU-Mix actually decreases to a 40-fold expansion in the IMDM control group, whereas a 500-fold expansion is observed in the LPCM treated group.

These results are further confirmed by enumeration of CD34+, CD38− cells exiting the day 7 and day 13 liquid cultures. In control cultures, the proportion of CD34+, CD38− cells at day 7 are 40-fold expanded and at day 13 are 23-fold expanded. In contrast, cultures that are supplemented with LPCM have an increased expansion rate in that at day 7 a 55-fold expansion is observed, whereas at day 13 a 150-fold expansion is observed.

This example illustrates that LPCM has the ability to synergize with cytokines that are known in the art to act on early lineage hematopoietic stem cells. In order to demonstrate the biological activity of expanded precursors, as well as to validate the possibility that LPCM actually maintains and expands hematopoietic stem cells with in vivo activity, fresh CD34 cells isolated from the cord blood, as well as after 7 and 13 days of culture in the conditions described above, as assessed in the SCID-repopulating assay NOD-SCID mice (Jackson Laboratories) are sublethally irradiated with 350 rads from a Cesium137 source. CD34 cells from the 3 respective timepoints are administered to 5 groups of mice, 10 mice per group, through tail vein injection. Group 1 receives $1 \times 10^5$ freshly isolated CD34 cells, Group 2 receives the same amount of cells that have been cultured for 7 days in liquid culture with IMDM control supplemented media, Group 3 receives the same amount of cells that have been cultured for 7 days in liquid culture with LPCM, Group 4 receives cells from day 13 liquid culture, with IMDM control media, and Group 5 receives cells from day 13 liquid culture supplemented with LPCM. Assessment of engraftment is made at 11 weeks by sacrificing the murine recipients, collecting bone marrow from the femur and tibia, and detection of the human specific CD45 marker in the murine bone using flow cytometry. While Group 1 possesses undetectable levels of human leukocytes. Groups 2 and 4 possess approximately 2% and 4% human leukocytes, respectively. Groups 3 and 5 possess approximately 13% and 21% human leukocytes, respectively. Furthermore, double staining with CD34 and human CD45 suggests that only Groups 3 and 5 possess detectable levels of human hematopoietic stem cells. This suggests that LPCM possesses the important activity of allowing expansion of a human hematopoietic cell population capable of efficient activity in vitro and in vivo.

Example 8

Expansion of Tolerogenic Dendritic Cells

It is known that dendritic cells can act both as immune stimulators or as immune suppressors. Unfortunately, clinical use of immune suppressive dendritic cells is hampered by inability to expand large enough numbers for therapeutic use. This is due to the fact that numerous dendritic cell-expanding regimens cause activation, leading to loss of tolerogenic properties. Accordingly in this experiment we seek to generate expanded numbers of dendritic cells with a tolerogenic phenotype.

Bone marrow cells are flushed from the femurs and tibias of C57/BL6 mice (Jackson Laboratories). Erythrocytes are lysed using lysis buffer, washed in PBS and cultured at 2×10⁶ cells/well in 24-well plates (Corning Glass, Corning, N.Y.) in 2 ml RPMI 1640 (Life Technologies, Ontario, Canada) supplemented with 10% FCS (Life Technologies), 100 U/ml of penicillin, 100 µg/ml of streptomycin, 50 µM of 2-ME (Life Technologies), 10 ng/ml of murine rGM-CSF (Peprotech, Rocky Hill, N.J.), 10 ng/ml of IL-4 (Peprotech) and the NF-kappa B inhibitor LF15-0195 (LF) at a concentration of 5 µg/ml. Cultures in which non-tolerogenic, conventional DC are desired do not contain LF, and agent previously demonstrated as a generator of tolerogenic DC (Ichim, supra; Yang, et al., 2003, *J Leukoc Biol* 74:438-447, each of which is incorporated by reference herein in its entirety). Nonadherent cells are removed after 48 h of culture, and fresh medium is added every 48 h. In some wells control RPMI is added at a volume of 1:4, whereas in other wells LPCM generated using RPMI as a base is added at the same concentration. After 7 days of culture, DC numbers are quantified by expression of the marker CD11c using flow cytometry. A 4-fold higher number of CD11c+ cells are extracted from cultures that were supplemented with LPCM as opposed to control media. Assessment of tolerogenic function is performed in vitro by observing upregulation of costimulatory molecules in response to treatment with 10 ng/ml TNF and 10 ng/ml LPS. While DC generated in absence of LF were capable of upregulating expression of CD40, CD80 and CD86 after activation, DC generated under the cover of LF, both with or without LPCM are resistant to upregulation of these molecules. Functional demonstration that tolerogenic DC raised with LPCM supplementation actually are tolerogenic is demonstrated by inability of these cells to stimulate a mixed lymphocyte reaction.

Varying numbers of DC are seeded in triplicate in a flat-bottom 96-well plate (Corning) for use as stimulator cells. DC are of the C57/BL6 strain and are grown either in the absence of LF, with LF but no LPCM, or with LF and LPCM. T cells are prepared from spleens of BALB/c and isolated by T cell enrichment columns (R&D Systems, Minneapolis Minn.). T cells (1-5×10⁵/well) are added to the DC cultures, with the final MLR taking place in 200 µl of RPMI 1640 (Life Technologies) supplemented with 10% FCS (Life Technologies), 100 U/ml of penicillin (Life Technologies), and 100 µg/ml of streptomycin (Life Technologies). Cells are cultured at 37° C. in a humidified atmosphere of 5% $CO_2$ for 3 days, and pulsed with 1 µCi of [3H]thymidine (Amersham Pharmacia Biotech) for the last 16 h of culture. Cells were harvested onto glass fiber filters, and the radioactivity incorporated was quantitated using a Wallac Betaplate liquid scintillation counter. Results indicate that while DC raised in absence of LF are potent stimulators of allogeneic T cell proliferation, DC raised with LF, either in the presence or absence of LPCM, are non-stimulatory.

In order to demonstrate functional tolerogenicity in vivo, control non-LF treated DC, LF-treated DC and LF+LPCM DC of the C57/BL6 strain are injected at a concentration of 10 million CD11c+ cells into BALB/c recipients 7 days prior to heterotopic cardiac transplantation with C57/BL6 grafts. Subsequent to grafting survival of transplanted hearts is 6 days in the non-LF treated DC recipients, whereas it is 18 days in the LF-treated DC recipients and 24 days in the LF-treated+LPCM treated recipients.

Example 9

LPMC in Treatment of Stroke

C57BL/6 (Jackson Laboratory) mice weighing approximately 25 grams each are given free access to food and water before and during the experiment. Animals are acclimated to the laboratory environment for 1 week prior to experimentation. Four groups of 10 mice each are treated by intravenous infusion as follows: Group 1 vehicle, Group 2 FGF-1 (10 mg/kg), Group 3 LPCM (100 U/kg), Group 4 FGF-1 (10 mg/kg) and LPCM (100 U/kg). Mice were infused intravenously, 1 hour after the initiation of ischemia. LPCM is generated, concentrated, and Units of activity are quantified as described in Example 4.

Each mouse is subjected to one hour of cerebral ischemia followed by 24 hours of reperfusion. At the end of the ischemic period, animals are treated as described in the above paragraph and at 14 days are examined for infarct volume. Each mouse is anesthetized and a thermistor probe is inserted into the rectum to monitor body temperature, which is maintained at 36-37° C. by external warming. The left common carotid artery (CCA) is exposed through a midline incision in the neck. The superior thyroid and occipital arteries are electrocoagulated and divided. A microsurgical clip is placed around the origin of the internal carotid artery (ICA). The distal end of the ECA (external carotid artery) is ligated with 6-0 silk and transected. A 6-0 silk is tied loosely around the ECA stump. The clip is removed and the fire-polished tip of a 5-0 nylon suture (poly-L-lysine coated) is gently inserted into the ECA stump. The loop of the 6-0 silk is tightened around the stump and the nylon suture is advanced approximately 11 mm (adjusted for body weight) into and through the internal carotid artery (ICA) after removal of the aneurysm clip, until it rests in the anterior cerebral artery (ACA), thereby occluding the anterior communicating and middle cerebral arteries. The animal is returned to home cage after removal from anesthesia. After the nylon suture is been in place for 1 hour, the animal is re-anesthetized, rectal temperature is recorded, the suture is removed and the incision closed.

Neurological deficits are assessed 14 days after ischemia based on a scale from 0 (no deficits) to 4 (severe deficits) as commonly used in the discipline. Neurological scores are as follows: 0, normal motor function; 1, flexion of torso and contralateral forelimb when animal is lifted by the tail; 2, circling to the contralateral side when held by the tail on a flat surface, but normal posture at rest; 3, leaning to the contralateral side at rest; 4, no spontaneous activity.

For infarct volume determination after behavioral testing, the animals are anesthetized with an intraperitoneal injection of sodium pentobarbital (50 mg/kg). The brains are removed, sectioned into 4 2-mm sections through the infracted region and placed in 2% triphenyltetrazolium chloride (TTC) for 30 minutes at 24 hours. Subsequently, the sections are placed in 4% paraformaldehyde over night. The infarct area in each section is determined with a computer-assisted image analysis system, consisting of a Power Macintosh computer equipped with a Quick Capture frame grabber card, Hitachi CCD camera mounted on a camera stand. NIH Image Analysis Software, v. 1.55 is used for quantification of image data. The images are captured and the total area of infarct is determined over the sections. A single operator blinded to treatment status performs all measurements. Summing the infarct volumes of the sections calculates the total infarct volume.

At day 14 after induction of ischemia animals are assessed by a blinded observer for neurological deficits based on the scale of 0 to 4 described above. Animals in Group 1 (vehicle control) have an average score of 3.3 0.335; Animals in Group 2 (FGF-1) have an average score of 3.0±0.576; Animals in Group 3 (LPCM) have an average score of 2.2±0.889; Animals in Group 4 (LPCM+FGF-1) have an average score of 0.4±1.023. This synergistic protective effect seen between FGF-1 and LPCM, is further supported by assessment of infarct size. According to present reduction in infarct size compared to the vehicle control group (Group 1), mice treated with FGF-1 alone (Group 2) had a reduction of 11%±2.52, mice treated with the LPCM alone (Group 3) had a reduction of 26%±1.34, and mice treated with the combination of FGF-1 and LPCM (Group 4) had a reduction in infarct size of 78%.

Example 10

LPMC Augmentation of Cord-Blood Reconstitution After Nuclear Incident

A terrorist "dirty bomb" nuclear attack on a populated city occurs exposing 100 individuals to an estimated 10 Gy Eq of neutron and gamma irradiation. All 100 patients presented with symptoms of acute radiation syndrome including severe pancytopenia. Based on previous experiences (Nagayama, et al., 2002. *Int J Hematol* 76:157-164, which is incorporated by reference herein in its entirety), and the lack of sibling related donors or possibility of autotransplantation, the use of cord blood as a hematopoietic graft is performed after HLA-matching allowing for only one allele mismatch. Pretransplantation conditioning consists of antithymocyte equine 3-globulin alone (2.5 mg/kg for 2 consecutive days), and GVHD prophylaxis consists of the combined use of cyclosporine A (CyA) and methylprednisolone (mPSL). Patients are administered $3 \times 10^7$ nucleated cord blood cells per kilogram through intravenous infusion. All patients are administered filgrastim (neupogen) at a concentration of 10 μg/kg/day for 14 days in order to accelerate leukocytic recovery. Of the 100 patients, 50 receive concurrently with filgrastim, a concentration of 250 Units of LPCM/kg/day. LPCM is prepared under GMP conditions based on the description of Example 4. At day 15 after cellular transplantation, 23% of patients treated with filgrastim alone have granulocytic counts of more than 500/mm$^3$. In contrast, 100% of the patients receiving the combination of filgrastim and LPCM have granulocytic counts of more than 500/mm$^3$ by day 12 post transplantation.

Chimeric hematopoiesis was observed at day 50 in 46% of patients treated with filgrastim alone, whereas 100% of patients receiving the combination had achieved this milestone. Additionally, opportunistic infections are predominantly associated with the patient group that received filgrastim alone.

This example suggests the use of LPCM as an adjuvant agent to standard hematopoiesis stimulating regimens. Additionally, although GVHD is not observed in any of the patients in the prior example, most likely due to the low levels of cord blood cells administered, higher doses of cord blood cells can predispose to this. Accordingly, LPCM can be used in combination with immune suppressive cytokines to preferential stimulate expansion of natural immune regulatory cell subsets.

Example 11

LPMC Augmentation of Endogenous Endothelial Stem Cells for End Stage Angina

Twelve patients with advance angina, as defined by the Seattle Angina Questionnaire and the Canadian Cardiovascular Society Angina Classification scores III-IV are informed they are not eligible for surgical or medical intervention. Patients have either one/two/three vessel disease as determined by angiography as being greater than or equal to 70% narrowing of a major epicardial coronary artery such as the right circumflex artery, the left circumflex artery, or the left anterior descending artery. Alternatively, some patients have diffuse type of coronary artery disease as evidenced by the appearance on coronary angiography of multiple stenoses, multiple atherosclerotic plaques, and/or peripheral occlusion(s) of coronary vessel(s) with and without a history of myocardial infarctions. Areas of hypoperfusion are identified according angiographically. Patients are then subjected to a mini-thoracotomy procedure similar to the procedure utilized for transmyocardial revascularization in similar patient subsets (Lamy, A., 1997, *Evid Based Cardiovasc Med* 1:77, which is incorporated by reference herein in its entirety). Specifically, standard anesthesia with intubation is used according to institutional guidelines, the left anterior mini-thoracotomy is performed by a longitudinal incision of the pericardium anterior to the phrenic nerve with sutures fixing the pericardial edges thus elevating the heart. Identification of coronary arteries and target myocardial area of treatment is determined by previous angiography (either periphery of LAD- or LCX or RCA-branches, depending of preoperative findings). An intravenous application of beta-blockers can be used to lower heart rate if mandated according to institutional procedures and/or the preference of the surgeon.

According to the procedure pioneered by Stegmann, et al., 2000, *Herz* 25:589-599, which is incorporated by reference herein in its entirety, for intramyocardial administration of growth factors, a weight-adjusted dose of LPCM of 250 U/kg in saline is then injected, via a 27 gauge needle, into the myocardium at the target area. The area of occlusion/lesion, determined from the screening angiogram, is identified. The injection site is limited to an area within a 1 cm diameter around the area of occlusion/lesion. The needle is inserted at a 45° angle directly into the myocardium at a depth no greater than 1 cm. The axis of the needle is inserted toward the periphery of the coronary vascular bed. The surgeon is then to confirm that the LPCM was not injected into the ventricular cavum by needle aspiration. Pericardial closure with reabsorbable single sutures is conducted. Insertion of a pleural drain and closure of thoracic incision is made.

Patients are subsequently examined at 3 and 6 months using SPECT radionuclide imaging for perfusion of the treated areas. A progressive improvement in perfusion area is observed, as well as restoration of the Canadian Cardiovascular Society Anginal Classification score from an average of 3.4±0.893 to 1.2±1.052.

Example 12

Generation of Autologous Hematopoietic Stem Cells for Patients Lacking Donors

A patient with chronic myeloid leukemia is in need of a bone marrow transplant in order to destroy the advanced leukemia burden. Unfortunately a suitable donor is not found and the patient is not eligible for an autologous bone marrow transplant due to the high possibility of relapse due to leukemic contamination of the bone marrow. The novel procedure of cellular reprogramming using cytoplasmic extracts of undifferentiated embryonic stem cells is performed, using LPCM as an expansion factor. Specifically, bone marrow cells are isolated and plated in long term cultures under standard conditions using imatinib (0.5-1.0 μM for 72 h) and then mafosfamide (30-90 μg/ml for 30 min) followed by 2 weeks in culture with cytokines (100 ng/ml each of stem cell factor, granulocyte colony-stimulating factor and thrombopoietin) as described (Bhatia, et al., 2004, *Hematol Oncol Clin North*

*Am* 18:715-732, xi; Yang, et al. A novel triple purge strategy for eliminating chronic myelogenous leukemia (CIVIL) cells from autografts. *Bone Marrow Transplant*, e-published on Jan. 23, 2006, each of which is incorporated by reference herein in its entirety). Putatively purged cells are plated under low concentrations in liquid cultures containing LPCM in order to allow colony formation and proliferation. Cells are picked from each colony and assessed for the Philadelphia Chromosome using single cell RT-PCR to amplify the oncogenic bcr-abl transcript as described (Brail, et al., 1999, *Mutat Res* 406:45-54, which is incorporated by reference herein in its entirety). Cells are picked using a micropipette from colonies lacking expression of the bcr-abl and are prepared for reprogramming using embryonic stem cell extracts. The extracts are prepared according a modification to the method of Collas in U.S. Patent Application No. 2002/0142397, which is incorporated by reference herein in its entirety: Interphase cultured embryonic stem cells of the H-1 line are harvested by trypsinization and washed by centrifugation at 500 g for 10 minutes in a 10 ml conical tube at 4° C. The supernatant is discarded, and the cell pellet is resuspended in a total volume of 50 ml of cold PBS. The cells are centrifuged at 500 g for 10 minutes at 4° C. This washing step is repeated, and the cell pellet is resuspended in approximately 20 volumes of ice-cold interphase cell lysis buffer (20 mM Hepes, pH 8.2, 5 mM $MgCl_2$, 1 mM DTT, 10 μM aprotinin, 10 μM leupeptin, 10 μM pepstatin A, 10 μM soybean trypsin inhibitor, 100 μM PMSF, and optionally 20 μg/ml cytochalasin B). The cells are sedimented by centrifugation at 800 g for 10 minutes at 4° C. The supernatant is discarded, and the cell pellet is carefully resuspended in no more than one volume of interphase cell lysis buffer. The cells are incubated on ice for one hour to allow swelling of the cells. The cells are lysed by sonication using a tip sonicator. Cell lysis is performed until at least 90% of the cells and nuclei are lysed, which is assessed using phase contrast microscopy. The sonication time required to lyse at least 90% of the cells and nuclei can vary depending on the type of cell used to prepare the extract. Accordingly, microscopic evaluation of cellular morphology is performed to assess degree of sonication needed. The cell lysate is placed in a 1.5-ml centrifuge tube and centrifuged at 10,000 to 15,000 g for 15 minutes at 4° C. using a table top centrifuge. The tubes are removed from the centrifuge and immediately placed on ice. The supernatant is carefully collected using a 200 μl pipette tip, and the supernatant from several tubes is pooled and placed on ice. This cell extract is then aliquoted into 20 μl volumes of extract per tube on ice. The tube is then overlayed with mineral oil to the top. The extract is centrifuged at 200,000 g for three hours at 4° C. to sediment membrane vesicles contained. At the end of centrifugation, the oil is discarded. The supernatant is carefully collected, pooled if necessary, and placed in a cold 1.5 ml tube on ice. This supernatant quantified for protein content and is referred to as the "cellular extract" that will be used for the reprogramming of cells.

CD34+ cells grown in colonies not expressing the bcr-abl transcript are then permeabilized temporarily. Cells are harvested by picking the entire colony with a micropipette of 200 μl and are washed with PBS. Cells are incubated in Streptolysin O solution (see, for example, Maghazachi et al., 1997, *FASEB J.* 11(10)765-774, which is incorporated by reference herein in its entirety) for 15-30 minutes at room temperature. After either incubation, the cells are washed by centrifugation at 400 g for 10 minutes. This washing step is repeated twice by resuspension and sedimentation in PBS. Cells are kept in PBS at room temperature until use. The permeabilized CD34 stem cells are suspended in the embryonic stem cell derived reprogramming cytoplasmic extract (generated as described above) at a concentration of 300 cells per μl. An ATP generating system (2 mM ATP, 20 mM creatine phosphate, 50 μg/ml creatine kinase) and 100 μM GTP are added to the extract, and the reaction is incubated at 30-37° C. for up to two hours to promote translocation of factors from the extract into the cell and active nuclear uptake or chromosome-binding of factors. The reprogrammed cells are centrifuged at 800 g, washed by resuspension, and centrifugation at 400 g in PBS. The cells are resuspended in culture medium containing 20-30% fetal calf serum (FCS) and incubated for 1-3 hours at 37° C. in a regular cell culture incubator to allow resealing of the cell membrane. The cells are then washed in regular warm culture medium (10% FCS) and cultured further using a concentration of 10 U/ml of LPCM in DMEM media, supplemented with IL-3 (20 ng/ml), IL-6 (250 ng/ml), SCF (10 ng/ml), TPO (250 ng/ml), and flt3-L (100 ng/ml). Media is exchanged 2-3 times per week. After 14 days of culture, cells are assessed by flow cytometry for expansion of early hematopoietic subtype, and by RT-PCR for expression of the bcr-abl oncogene. A potent expansion of CD34+ cells is obtained, and some cells express the embryonic stem cell marker SSEA-4. The culture is subsequently transferred to 250 ml bag culture and maintained until a concentration of $1 \times 10^7$ CD34+ cells are generated. Said cells are subsequently assessed for possible contamination and expression of bcr-abl. Cells are subsequently used for performing autologous bone marrow transplant.

Example 13

LPCM for Treatment of Critical Limb Ischemia

A group of 20 patients are chosen who present with Fountaine Grade III-IV critical limb ischemia, at risk of amputation. Area of atherosclerosis and ischemia is identified using angiography. Doppler scans reveal significant hypoperfusion, and in some areas almost complete ischemia. LPCM is generated as described in Example 4, in a DMEM base and administered to 10 of the patients, whereas the other 10 receive the DMEM vehicle without exposure to placenta. The formulation that is administered to the patients is reconstituted in saline with 3% human serum albumin to maintain protein stability. Desalting and batch testing is performed. Treated patients receive a total of 5 injections per week in areas identified as ischemic. Untreated control patients receive similar injections, but with vehicle alone. After 3 months of treatment initiation a clinical response is observed in 7 out of the 10 patients treated, whereas no responses is seen in the control group. Clinical response is classified as decrease in Fountaine Score status over 0.5 percent in combination with improvement in localized circulation as detected by angiographic examination performed by an operator blinded to the experiment.

One skilled in the art will appreciate that these methods and devices are and can be adapted to carry out the objects and obtain the ends and advantages mentioned, as well as those inherent therein. The methods, procedures, and devices described herein are presently representative of preferred embodiments and are exemplary and are not intended as limitations on the scope of the invention. Changes therein and other uses will occur to those skilled in the art which are encompassed within the spirit of the invention and are defined by the scope of the disclosure.

It will be apparent to one skilled in the art that varying substitutions and modifications can be made to the invention disclosed herein without departing from the scope and spirit of the invention.

Those skilled in the art recognize that the aspects and embodiments of the invention set forth herein can be practiced separate from each other or in conjunction with each other. Therefore, combinations of separate embodiments are within the scope of the invention as disclosed herein.

All patents and publications mentioned in the specification are indicative of the levels of those skilled in the art to which the invention pertains. All patents and publications are herein incorporated by reference to the same extent as if each individual publication was specifically and individually indicated to be incorporated by reference.

The invention illustratively described herein suitably can be practiced in the absence of any element or elements, limitation or limitations which is not specifically disclosed herein. Thus, for example, in each instance herein any of the terms "comprising," "consisting essentially of" and "consisting of" may be replaced with either of the other two terms. The terms and expressions which have been employed are used as terms of description and not of limitation, and there is no intention that in the use of such terms and expressions indicates the exclusion of equivalents of the features shown and described or portions thereof. It is recognized that various modifications are possible within the scope of the invention disclosed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the disclosure.

What is claimed is:

1. A method for the expansion or growth of stem cells without substantially inducing differentiation, the method comprising:

collecting cord blood from a human umbilical cord;

isolating CD34+ cells from the cord blood;

producing live placenta conditioned medium (LPCM) by incubating whole human placenta in a Dulbecco's modified Eagle medium (DMEM) in a sterile container, wherein the whole placenta is submerged;

isolating the LPCM; and contacting at least one CD34+ cell with a supplemented DMEM comprising the LPCM and a cytokine cocktail comprising 20 ng/ml IL-3, 250 ng/ml IL-6, 10 ng/ml stem cell factor, 250 ng/ml thrombopoietin, and 100 ng/ml Flt-3L, wherein the concentration of the LPCM in the supplemented DMEM is 50%.

2. The method of claim 1, wherein isolating CD34+ cells comprises a method selected from the group consisting of fluorescence activated cell sorting, magnet activated cell sorting, counterflow centrifugal elutriation, equilibrium density centrifugation, velocity sedimentation at unit gravity, and T lymphocyte depletion.

3. The method of claim 1, wherein incubating whole human placenta in a DMEM comprises a period of at least 24 hours.

4. The method of claim 1, further comprising decontaminating the isolated LPCM by a method selected from the group consisting of filtration, UV irradiation, X-ray sterilization, ozonation, and hyperthermia.

5. The method of claim 1, wherein contacting at least one CD34+ cell with a supplemented DMEM comprises a period of at least 24 hours.

6. The method of claim 1, wherein the supplemented DMEM comprises a growth factor selected from the group consisting of, IL-1, IL-7, G-CSF, GM-CSF, Epo, FGF-1, FGF-2, FGF-4, FGF-20, IGF, EGF, NGF, LIF, PDGF, bone morphogenic proteins (BMP), activin-A, VEGF, and forskolin.

* * * * *

UNITED STATES PATENT AND TRADEMARK OFFICE
CERTIFICATE OF CORRECTION

PATENT NO. : 8,895,299 B2
APPLICATION NO. : 12/823960
DATED : November 25, 2014
INVENTOR(S) : Neil H. Riordan It is certified that error appears in the above-identified patent and that said Letters Patent is hereby corrected as shown below:

Title Page

In column 1 (page 2, item 56) at line 11, Under Other Publications, change "H emopoietic" to --Hemopoietic--.

In column 1 (page 2, item 56) at line 47, Under Other Publications, change "pre-cology-forming" to --pre-colony-forming--.

In column 2 (page 2, item 56) at line 17, Under Other Publications, change "Macrophase" to --Macrophage--.

In column 2 (page 2, item 56) at line 19, Under Other Publications, change "Preipheral" to --Peripheral--.

In the Specification

In column 1 at line 45, Change "el al.," to --et al.,--.

In column 2 at line 6, Change "blastocyte" to --blastocyst--.

In column 5 at line 19, Change "consitutively" to --constitutively--.

In column 9 at line 45, Change "entirety)" to --entirety).--.

In column 10 at line 10, Change "mesenchphalic" to --mesencephalic--.

In column 10 at line 59, Change "exanguinated" to --exsanguinated--.

In column 11 at line 4, Change "intravasular" to --intravascular--.

In column 16 at line 16, Change "environment" to --environment.--.

In column 16 at line 29, Change "GM-C SF." to --GM-CSF.--.

In column 19 at line 45, Change "TRA-1-81" to --TRA-1-81,--.

In column 20 at line 15, Change "Dublecco's" to --Dulbecco's--.

In column 20 at line 35, Change "intravasular" to --intravascular--.

Signed and Sealed this
Twenty-eighth Day of July, 2015

Michelle K. Lee
*Director of the United States Patent and Trademark Office*

CERTIFICATE OF CORRECTION (continued)
U.S. Pat. No. 8,895,299 B2

In column 20 at line 37, Change "intravasular" to --intravascular--.

In column 20 at line 39, Change "intravasular" to --intravascular--.

In column 21 at line 57, Change "differentation." to --differentiation.--.

In column 22 at line 56, Change "fromG-CSF," to --from G-CSF,--.

In column 23 at line 26, Change "allogenenic" to --allogeneic--.

In column 23 at line 34, Change "allogenenic" to --allogeneic--.

In column 25 at line 42, Change "erthrocytic," to --erythrocytic,--.

In column 25 at line 42, Change "megakarocytic," to --megakaryocytic,--.

In column 26 at line 23, Change "Nall" to --Natl--.

In column 27 at line 32, Change "Program):" to --Program) :--.

In column 29 at line 24, Change "glucocorticords," to --glucocorticoids,--.

In column 29 at line 39, Change "are" to --art--.

In column 30 at line 58, Change "xoonosis." to --zoonosis.--.

In column 30 at line 62, Change "deaggrated" to --disaggregated--.

In column 32 at line 53, Change "Inc)" to --Inc).--.

In column 33 at line 30, Change "more," to --more.--.

In column 36 at line 8, Change "culture," to --culture.--.

In column 37 at line 24, Change "polyhydroxpriopionic" to --polyhydroxypropionic--.

In column 39 at line 23, Change "polyetheylene" to --polyethylene--.

In column 41 at line 47, Change "pulsitile" to --pulsatile--.

In column 41 at line 49, Change "continous" to --continuous--.

In column 42 at line 57, Change "deaggregated" to --disaggregated--.

In column 49 at line 2, Change "(CIVIL)" to --(CML)--.

In column 49 at line 17, Change "entirety:" to --entirety.--.

In the Claims

In column 52 at line 35 (approx.), In Claim 6, change "of," to --of--.